(12) United States Patent
Regimand

(10) Patent No.: US 6,321,589 B1
(45) Date of Patent: Nov. 27, 2001

(54) METHODS AND APPARATUS FOR SEALING A POROUS MATERIAL SAMPLE FOR DENSITY DETERMINATION USING WATER DISPLACEMENT METHODS AND ASSOCIATED SURFACE CONFORMAL RESILIENT COMPRESSIBLE BAGS

(75) Inventor: Ali Regimand, Raleigh, NC (US)

(73) Assignee: InstroTek, Inc., Raleigh, NC (US)

( * ) Notice: Subject to any disclaimer, the term of this patent is extended or adjusted under 35 U.S.C. 154(b) by 0 days.

(21) Appl. No.: 09/340,105

(22) Filed: Jun. 25, 1999

(51) Int. Cl.[7] ........................................... G01N 9/00

(52) U.S. Cl. .......................... 73/32 R; 383/42; 702/137; 73/437

(58) Field of Search ..................... 73/32 R, 433, 73/437; 383/42; 702/137

(56) References Cited

U.S. PATENT DOCUMENTS

| 4,083,228 | 4/1978 | Turner et al. ................ 73/32 R |
| 5,606,126 | * 2/1997 | Glenville ..................... 73/433 |
| 5,760,293 | 6/1998 | Orr et al. ................... 73/32 R |

FOREIGN PATENT DOCUMENTS

| 2004530A | 8/1971 | (DE) . |
| 0936451A1 | 8/1999 | (EP) . |
| 62269040A | 5/1988 | (JP) . |
| 10010032A | 1/1998 | (JP) . |

OTHER PUBLICATIONS

Stephens, "Bituminous Mix Density by Coated Specimen," Project No. 67–5, Connecticut Dept. of Transportation (Jan. 1973).*

Dept. of Defense, "Standard Test Method for Bulk Specific Gravity and Density of Non–Absorptive Compacted Bituminous Mixtures," ASTM Standards, Designation: D2726, pp. 242–244 (Oct. 1996).*

(List continued on next page.)

Primary Examiner—Richard A. Moller
(74) Attorney, Agent, or Firm—Myers Bigel Sibley & Sajovec

(57) ABSTRACT

Water-resistant preformed resilient bags are applied to a porous material specimen having a coarse external surface to provide for more consistent measurement results in water displacement tests. The preformed bag is configured to collapse and substantially conform to the material specimen's external surface and to provide planar collapsed portions extending away from the specimen. The preformed bags are precision manufactured and each applied to a respective specimen in a manner in which the bag consistently displaces the same volume of water when used in water displacement tests over many specimens. The volume of the bag can be accounted for when obtaining the volume of the specimen. The method of sealing the specimen includes inserting the specimen into a preformed bag and collapsing and sealing the bag such that is conformal to the external surface of the specimen. The method can provide a preferred operating vacuum pressure corresponding to the specimen type (such as porosity or coarseness) which can automatically direct the operational parameters of the bag sealing operation. The system includes a preformed bag configured to receive a material specimen therein, a vacuum apparatus for removing the air from the bag, and a sealing means for sealing the bag. In one embodiment the vacuum apparatus includes an integrated scale for measuring various weights associated with the specimen for liquid density determinations.

66 Claims, 19 Drawing Sheets

OTHER PUBLICATIONS

Dept. of Defense, "Standard Test Method for Bulk Specific Gravity and Density of Compacted Bituminous Mixtures Using Paraffin–Coated Specimens," ASTM Standards, Designation: D1188, pp. 118–120 (Oct. 1996).*

Birello et al., "Advance in density measurements by means of an automatic hydrostatic weighing system of 100 g capacity," Measurement, vol. 7, No. 4, pp. 157–162 (Oct.–Dec. 1989).

Wolf, B., "Application of hydrostatic weighing to density determination of tiny porous samples," Rev. Sci. Instrum, vol. 66 (3), pp. 2578–2581 (Mar. 1995).

PCT International Search Report, International Application No. PCT/US00/17150 mailed Oct. 20, 2000.

* cited by examiner

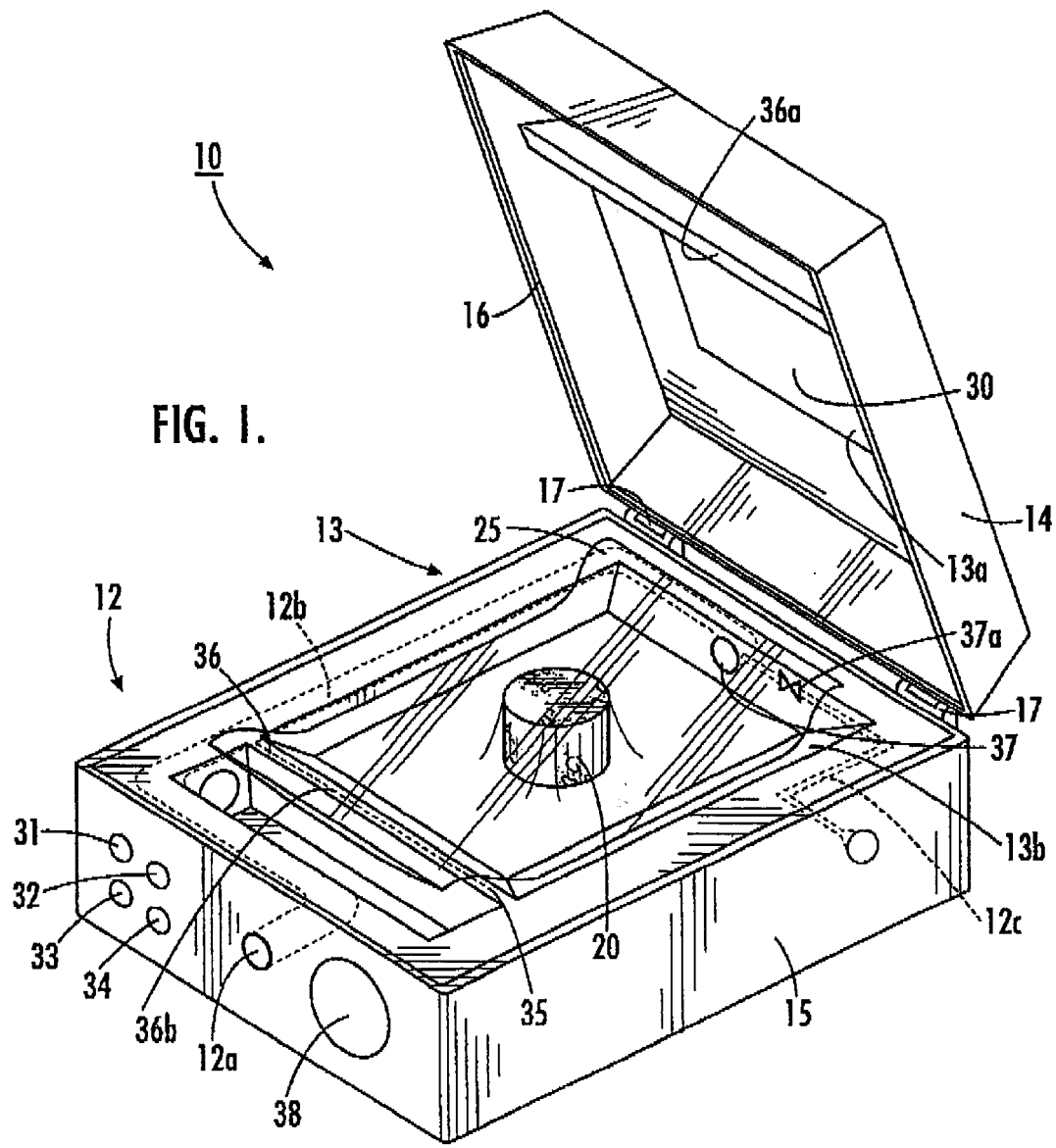

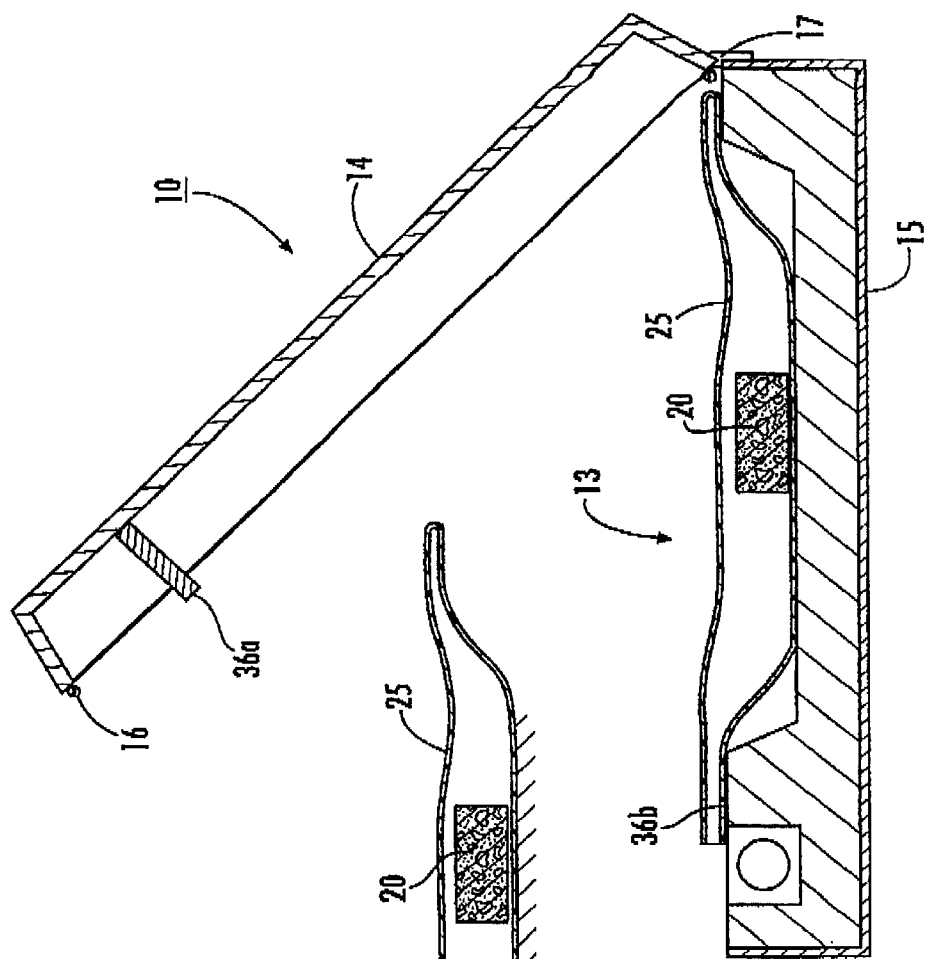
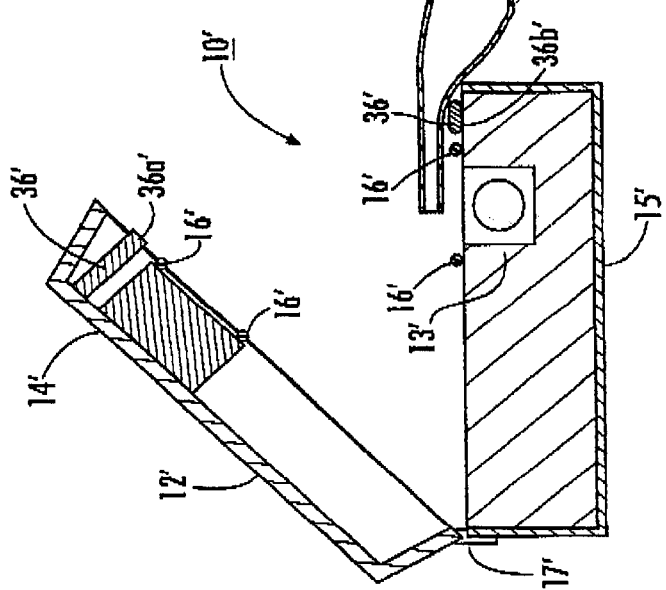

CALIBRATION OF BAG DENSITY

| SAMPLE # | STD WT IN AIR | STD WT IN H20 | SEALED IN AIR | SEALED IN H20 | WT OF BAG | VOL OF STD | VOL OF STD+BAG | VOL OF BAG | DENSITY OF BAG |
|---|---|---|---|---|---|---|---|---|---|
| STD1 | 2498.6 | 1576 | 2532.3 | 1565.5 | 33.7 | 925.38 | 969.71 | 44.33 | 0.760 |
| STD2 | 3751.5 | 2365.7 | 3785.2 | 2354 | 33.7 | 1389.97 | 1435.51 | 45.54 | 0.740 |

CALCULATION OF CORE DENSITY

| SAMPLE # | CORE WT IN AIR | SEALED WT IN AIR | SEALED WT IN H20 | TOTAL VOL | VOL OF BAG | VOL OF CORE | DENSITY OF CORE (gm/cm³) | DENSITY OF CORE (pcf) |
|---|---|---|---|---|---|---|---|---|
| SMA-1 | 4501.4 | 4534.6 | 2480.1 | 2060.68 | 44.27 | 2016.42 | 2.232 | 139.4 |
| SMA-2 | 4603.4 | 4636.9 | 2569.5 | 2073.62 | 44.67 | 2028.95 | 2.269 | 141.6 |
| SMA-3 | 4726.9 | 4760.5 | 2612 | 2154.96 | 44.80 | 2110.16 | 2.240 | 139.8 |
| FG-SP-1 | 4680.3 | 4715.2 | 2677.1 | 2044.23 | 46.53 | 1997.70 | 2.343 | 146.3 |
| FG-SP-2 | 4709.2 | 4743.6 | 2680 | 2069.81 | 45.87 | 2023.94 | 2.327 | 145.3 |
| FG-SP-3 | 4728.3 | 4763.7 | 2721.9 | 2047.94 | 47.20 | 2000.74 | 2.363 | 147.5 |
| CG-SP-2 | 4759.2 | 4793.3 | 2679 | 2120.66 | 45.47 | 2075.20 | 2.293 | 143.2 |
| CG-SP-3 | 4771.4 | 4805.7 | 2685.2 | 2126.88 | 45.73 | 2081.15 | 2.293 | 143.1 |
| CG-SP-1 | 4771.1 | 4805.8 | 2683.7 | 2128.49 | 46.27 | 2082.22 | 2.291 | 143.0 |
| CG-SP-1 | 4771.1 | 4805.6 | 2685.8 | 2126.18 | 46.00 | 2080.18 | 2.294 | 143.2 |
| CG-SP-1 | 4771.1 | 4804.6 | 2685.7 | 2125.28 | 44.67 | 2080.61 | 2.293 | 143.2 |
|  |  |  |  |  |  | STD.DEV | 0.001 | 0.074 |
| OGFC-1 | 3531.3 | 3564 | 1849 | 1720.16 | 43.60 | 1676.56 | 2.106 | 131.5 |
| OGFC-2 | 3806.5 | 3839.7 | 2015.2 | 1829.99 | 44.27 | 1785.72 | 2.132 | 133.1 |
| OGFC-3 | 3770.6 | 3805.1 | 1976.5 | 1834.10 | 46.00 | 1788.10 | 2.109 | 131.6 |

FIG. 21.

DETERMINE Corelok™ SEALANT MATERIAL DENSITY USING ALUMINUM STANDARDS ("As")

| SAMPLE # | A<br>As WEIGHT<br>IN AIR | B<br>As WEIGHT<br>IN WATER | C<br>SEALED As<br>WEIGHT IN<br>AIR | D<br>SEALED As<br>WEIGHT IN<br>WATER | E<br>C-A | F<br>B-A<br>0.997 | G<br>C-D<br>0.997 | H<br>G-F | I<br>E/H |
|---|---|---|---|---|---|---|---|---|---|
| | | | | | | | | | |
| | | | | | | | | | |
| | | | | | | | | | |
| | | | | | | | | | |
| | | | | | | | | | |

DETERMINE CORE DENSITY USING Corelok™ SEALANT TECHNIQUE

| SAMPLE # | J<br>CORE WEIGHT<br>IN AIR | K<br>Corelok™<br>CORE WEIGHT<br>IN AIR | L<br>Corelok™<br>CORE WEIGHT<br>IN WATER | M<br>K-J<br>0.997 | N<br>K-J<br>I | O<br>M-N | P<br>(CORE<br>DENSITY)<br>J/O |
|---|---|---|---|---|---|---|---|
| | | | | | | | |
| | | | | | | | |
| | | | | | | | |
| | | | | | | | |
| | | | | | | | |

FIG. 22.

METHODS AND APPARATUS FOR SEALING A POROUS MATERIAL SAMPLE FOR DENSITY DETERMINATION USING WATER DISPLACEMENT METHODS AND ASSOCIATED SURFACE CONFORMAL RESILIENT COMPRESSIBLE BAGS

FIELD OF THE INVENTION

The present invention is related to methods and devices used to determine the specific gravity or density of material specimens by water displacement methods. This invention is particularly suitable for use with material specimens which exhibit irregular or coarse exterior surfaces and porosity or voids, such as samples of compacted bituminous mixtures, soil samples, and concrete specimens used in the structure, infrastructure, and/or underlayment of many roadways.

BACKGROUND OF THE INVENTION

In the construction industry, a water displacement test is used to establish the bulk material density associated with the acceptability of the material durability used to form the pavement or underlayment of roadways or other construction or building projects. For example, most roadways consist of a plurality of materials and layers including different types of aggregates, rocks, stones, gravel, or other materials which are compacted together to form the foundation and/or structure for the roadway surface and construction structures. These material compositions can be described as "compacted mixtures". The composition of the compacted mixture is generally considered to be an important factor in the service life of the construction project. In order to assure that the construction projects (such as a particular roadway or substructure) exhibit sufficient performance characteristics and useful service lives, most construction projects are constructed to certain minimum build specifications or standards. One important standard used to assess the acceptability of the compacted mixture, particularly in the asphalt and soil industries, is a bulk specific gravity and density measurement of the compacted mixture.

A typical standard test method used to assess the bulk density of the compacted bituminous (asphalt) mixture is ASTM D2726. During evaluation, a field sample or laboratory molded sample is obtained. The pavement specimens are usually taken from pavements in the field with a core drill, diamond or a carborundum saw, and the like. In any event, the core specimen, whether from the field or molded in the laboratory, is typically in the shape of a cylinder. As such, the field specimen typically exhibits a rough uneven exterior surface. In order to preserve the integrity of the core specimen during and after removal from pavements or molds (and during testing), care is taken to avoid distortion, bending, or cracking of the specimens.

Generally described, the ASTM D2726 test method involves measuring the specimen's weight, both in air and in water. More particularly, during this analysis, three different weights of the specimen are measured; a weight in water, a dry weight, and a saturated surface dry weight. The difference between the sample's weight in the air and in the water is equal to the weight of the water displaced (which can be measured, this determines the volume of the water displaced) and saturated surface dry weight can be used to ascertain the amount of water absorbed by the sample. Since the volume of displaced water is known, the specific gravity of the sample can be determined. The test method results can be used to determine the unit weight of compacted construction material (typically dense) mixtures. This method is generally accepted as being accurate for smooth and/or non-porous samples. Indeed, the method is used around the world to determine the conformance to various regulatory specifications, both for prepared laboratory samples and field extracted samples.

The ASTM D2726 test method is not recommended for use with samples that contain open or interconnecting voids or that absorb more than 2% of water by volume, or both, as determined by saturated surface dry weight, e.g., "porous samples". Using this test method for porous samples can provide unreliable density measurements. This is attributed to the variable amount of water absorbed by the porous sample which can result in an inaccurate volume determination and, thus, an inaccurate and unreliable density determination.

Presently, specification standards require that the porous samples be measured differently from the ASTM D2726 test method. Typically, ASTM D1188 is recommended for use if the percent water absorbed by the specimen or sample exceeds 2%. ASTM D1188 is directed to the use of "paraffin-coated specimens" to seal the sample to prevent water infiltration into the porous samples whose specific gravity is to be determined by water displacement methods. In one paraffin application, in order to coat the sample, the sample is submerged into hot-melted paraffin wax and pulled out and cooled allowing the paraffin to solidify and form a shell around the sample. The density is then determined using the water displacement method. Unfortunately, the thickness of the paraffin layer can be inconsistent, which can produce variability in the measurement results. Further, penetration of the wax into the voids themselves can result in inflated density measurements. In addition, paraffin wax is difficult, if not impossible, to completely remove once applied, and the specimen is generally rendered unsuitable for further analysis. Further, the presence of a supply of melted hot wax can introduce safety hazards for laboratory personnel.

ASTM D1188 describes using Parafilm®, an elastomeric self-sealing moisture proof film obtainable from most scientific suppliers. As described, three pieces of Parafilm® are cut from the roll, two 100×100 mm (4×4 in) and one 100×200 mm (4×8 in). The backing is pulled off the backside of one of the 100×100 pieces and opposite sides of the film are grasped to stretch the film (carefully, without creating holes) and then placing the stretched film over one end of the specimen and pressing the sides of the stretched film around the sample. The specimen is turned over and positioned on a cushioned foam mat and the other end is wrapped with another piece of the stretched Parafilm®. Another specimen is used to force the air pockets from both surfaces by pressing against a piece of foam which is positioned on top of the wrapped specimen. A sharp knife is used to trim the excess film, keeping a minimum of 15 mm (0.5 in) on the side of the specimen at each end. The third piece of film is then applied. This elastomeric film method determines the "apparent specific gravity of Parafilm®" by using the specific gravity of an aluminum calibration cylinder before and after it is wrapped with Parafilm® as noted above. Unfortunately, this sealing method is relatively labor intensive. Further, the amount of Parafilm® used during the wrap as well as how it is stretched over the sample can be inconsistent, which can result in measurement inconsistencies. In addition, air can be trapped under the film during the film wrapping process. Still further, the film is susceptible to puncture both during application and during actual testing potentially allowing water to enter through the puncture. Clearly, either the trapped air or puncture can adversely affect the reliability of this method.

Another method for measuring the bituminous mix density by water displacement with coated specimens is proposed by Jack E. Stephens, in a report entitled "Bituminous Mix Density by Coated Specimen," Project Number 67-5, Connecticut Department of Transportation (January 1973). This method proposes using a vacuum pump and two sheets of acetate to wrap the specimen. The first acetate or plastic sheet is apparently heated and held in tension in position while the sample is raised until it contacts the plastic. The rising specimen enters the center of the tensioned sheet and forces the plastic to wrap around the upper surface and the sides of the specimen. The tensioned material provides a surplus of material extending from both sides when the first sheet is released from the tensioning members (plastic clamps). This surplus material is then trimmed, leaving the lower surface and a minor portion of the sides exposed. The sample is then turned such that the lower surface faces upward and a second sheet of acetate is wrapped over the remaining exposed surface, and the second sheet overlaps a portion of the first sheet along the sides. Again, the excess material of the second acetate sheet is trimmed. After trimming, the sample is enclosed in a shrink-wrap acetate material layer with a double layer of the acetate formed along its sides. This method also proposes using a heater when forming the plastic over the specimen, to soften the plastic to facilitate the molding of the (heated) soft plastic to the sample. Unfortunately the heating temperature and time of the plastic can affect the degree of the softness of the plastic, which, in turn, affects the adherence of the plastic to coarse, irregular, and porous samples, thereby undesirably introducing variations into the measurement. Again, this procedure can be relatively cumbersome and the amount of trim removed can vary from sample to sample, introducing possible measurement error. Further, without careful control of the amount of vacuum pulled on the sample, significant variability can occur in the density measurement. Also, the speed at which the sample is raised to contact the plastic can cause the specimen or sample to puncture the sealing material allowing water to leak into the sample during liquid displacement testing. In addition, asphalt softens at approximately 150° F. Heating the plastic can soften the asphalt layer at the surface and thereby change or alter the composition or condition of the sample during the water displacement test and also for any subsequent tests conducted subsequent to the liquid displacement density determination.

In recent years, the Federal Highway Administration ("FHA") has worked to improve the service life of bituminous pavements. As a result of a recent 5-year test, the FHA has recommended using compacted bituminous mixtures with larger aggregate size proportions. This larger aggregate size is believed to improve pavement performance and service life. Unfortunately, due to the use of larger aggregates, the asphalt specimens now prepared in the lab or extracted from the field have coarse and porous compositions. Typically, the coarse and porous compositions include a larger than 2% variation in air weight compared to saturated surface dry weight. This variation will make these samples unsuitable for the unsealed evaluation and, according to the ASTM standards discussed above, require that such samples be evaluated by sealed water displacement methods.

OBJECTS AND SUMMARY OF THE INVENTION

It is therefore an object of the present invention to provide a reliable and easy to use method for determining the specific gravity and/or density of compacted bituminous material samples with water displacement evaluation techniques.

It is another object of the present invention to provide an improved method and device for sealing material specimens, including those exhibiting coarse surfaces and porous properties, to inhibit water infiltration into the sample when measuring specific gravity of that sample by water displacement methods.

It is an additional object of the present invention to provide a consistent and repeatable sealing method which minimizes laboratory labor efforts and can be easily used.

It is yet another object of the present invention to seal porous samples for water displacement evaluation in a manner which is relatively quick, provides accurate testing measurements, and which preserves the integrity of the sample such that it is suitable for further post-sealing test evaluation.

These and other objects of the present invention are provided by methods, encased samples, and systems which employ at least one preformed precision-manufactured sealable bag which is sized and configured to hold a compacted material sample therein. The preformed resilient bags are manufactured to be consistent in size (or sizes), and, thus, are configured to reliably displace a constant volume of water, without relying on an operator's shaping of the material onto the sample. The method and encased samples provide predictability in the sealing application and thus, more reliable water displacement measurement evaluations. During operation, the material specimen sample is conveniently inserted into the bag at the use point and the bag is then conformed to rest against the surface of the sample in a controlled manner, i.e., such as by manipulating the bag to a surface conformal configuration (the walls of the bag substantially conform to the sample's external perimeter surface profile) and sealed. Preferably, a vacuum apparatus with a preset time and/or pressure is used to collapse or deflate a chamber holding the bag (remove the excess air) and then the chamber is also preferably controllably exhausted (returned to atmospheric pressure) in a manner which gradually introduces the air therein to collapse the bag against the sample and, thus, provides an automatic and consistent sealed sample configuration corresponding to the sample type. The controlled exhaust rate can inhibit punctures as the bag walls conform to the side of the specimen gradually (as opposed to abruptly). Advantageously, no trimming of excess material is required and the variability due to operator input is minimized. Also, after the water displacement test, the sample's composition and structural integrity remains intact and the sample is thus available for further evaluation.

More particularly, a first aspect of the present invention is a sample specimen configuration for a dense material sample to inhibit liquid contacting the sample during liquid displacement tests. The sample specimen configuration comprises at least one preformed resilient bag having at least one sealed side and one opening formed therein and defining a holding chamber. The system also includes a material sample having an exterior surface contour positioned in the chamber of the preformed resilient bag. The preformed bag has a first non-sealed configuration and a second sealed configuration. In the second sealed configuration, the preformed bag is configured to substantially conform to the sample's exterior surface contour. In a preferred embodiment, the configuration is provided by a system which includes a vacuum apparatus used to encase and conform the bag to the surface of the sample and a heater element used to seal the open edge of the bag while the bag is under vacuum.

Another aspect of the present invention is a method for preparing a compacted sample for liquid displacement testing. The method comprises the steps of providing a preformed resilient bag with predetermined dimensions, the bag having a perimeter with a portion of the perimeter having an open portion formed therein. A material specimen is subsequently inserted into the bag and the bag open portion is sealed. The method also includes the step of encasing the material specimen within the bag such that a portion of the bag substantially conforms the exterior profile of the material specimen held therein to thereby form an encased specimen suitable for liquid displacement evaluation.

An additional aspect of the present invention is an apparatus for sealing a specimen. The apparatus comprises a preformed resilient bag defining a holding chamber therein and a compacted material sample having an exterior surface contour positioned in the chamber of the resilient bag. The bag has a first non-sealed configuration and a second sealed configuration. In the second configuration, the bag is configured to encase and substantially conform about the sample's exterior surface contour. The apparatus also includes a vacuum apparatus which is operably associated with the preformed bag holding the compacted material sample. In a preferred embodiment, the apparatus includes an air chamber with an air flow channel with an adjustable flow rate. In operation, and the bag collapses to conform to the exterior contour responsive to the controlled introduction of air into the air chamber after evacuation of same.

An additional aspect of the present invention is a reproducible puncture resistant water jacket for a compacted material specimen for use in water displacement density or specific gravity tests. The water jacket includes a preformed resilient bag structure having at least two co-joined sides. The structure is sized and configured to receive a compacted material specimen therein. As such, the bag structure has a first open configuration and a second sealed configuration. The bag structure core is conformal to the profile of the specimen in the second sealed configuration (i.e., a portion of the bag conforms to rest against the exterior of the specimen while the portions of the bag structure away from the specimen contacts the opposing wall surface). The bag structure is produced at a first site and completely sealed at a second site remote from the first site. Preferably, the bag structure is defined by a preformed bag with a single open side. It is also preferred that the bag structure be configured for puncture resistance such as with reinforcement regions, patches, or double bags.

Yet another aspect of the present invention is directed to a method for immersing a compacted mixture in a liquid displacement bath for determining the specific gravity of specimens. The method comprises the steps of inserting a material specimen having an exterior surface into a bag having at least one open side and encasing the specimen by collapsing a portion of the bag to substantially conform to the material specimen exterior surface. The method also includes sealing the bag to enclose the material specimen therein and placing the sealed collapsed bag with specimen in a liquid displacement bath. The volume of displaced water associated with the placing step is then measured. Preferably, the method also includes the step of establishing bag density values associated with a particular bag type and specimen type across a plurality of specimen thicknesses. This establishing step can be performed by using a plurality of reference standards with known densities (aluminum blocks) and different thicknesses to determine a mathematical model or relationship which can be programmed into a computer. This established relationship can be provided at the factory and not require an operator to determine the value at the point of test for each specimen in the laboratory.

An additional aspect of the present invention is a resilient container for a porous sample. The resilient container comprises a first layer of a first material. The first layer includes a first perimeter portion. The resilient container also includes a second layer of a second material configured to overlay the first layer. The second layer includes a second perimeter portion corresponding to the first perimeter portion. The first and second perimeter portions are co-joined along a major portion thereof defining an internal compressible chamber therebetween and edge portions which extend laterally outward from the chamber. A compacted material specimen is held in the chamber. The first and second layers are formed of a resilient material such that the chamber has a first collapsed position and a second non-collapsed position, the collapsed position corresponds to the chamber being sealed with the compacted material specimen positioned therein. Preferably, the first and second layer materials are selected to provide oxygen resistant shielding and/or puncture resistance.

Another aspect of the present invention is a method of preparing a porous sample for use in a water displacement testing. The method comprises the steps of inserting a porous sample having an exterior profile into a preformed bag and collapsing the preformed bag to contact the exterior profile of the porous sample. The preformed bag is sealed to enclose the porous sample therein, thereby providing a sealed sample.

Yet an additional aspect of the present invention is directed to a method and computer program product for sealing a material specimen in a preformed bag. The computer program product comprises a computer readable storage medium having computer readable program code means embodied in the medium, the computer-readable program code means comprises computer readable program code means for accepting user input information associated with identifying the material specimen and computer readable program code means for comparing the identified material specimen with predetermined operating parameters for directing the operation of a vacuum apparatus operably associated with the preformed bag holding the material specimen. The product also includes a computer readable program code means for directing the operation of the vacuum apparatus corresponding to the operating parameters associated with the identified material specimen to compress the preformed bag to substantially conform to the exterior shape of the material specimen. Preferably, the computer program product also includes a computer readable program code means for accepting user input information associated with the identification of the preformed bag being sealed (i.e., product identification number which relates to bag design parameters such as size, material type, etc.). In a preferred embodiment, the computer program product further includes a computer readable program code means for providing a preformed bag adjustment number for use in specific gravity or density measurement calculations associated with water displacement tests and a computer readable program code means for printing information to a printer.

It is an additional aspect of the present invention to provide a semi automated system for establishing specific gravity in compacted specimens using liquid displacement testing. The system includes a vacuum apparatus with an internal vacuum chamber and a first scale positioned integral to the vacuum apparatus such that it can provide a dry weight measure of a sealed specimen held therein. The system also includes a liquid displacement bath and a second scale operably associated with the liquid displacement bath.

The system further includes a computer means operably associated with the first scale, the second scale, and the vacuum apparatus. The computer means includes a computer program product which has a computer readable program code means for calculating the specific gravity of a compacted material specimen corresponding to data directly input into the computer means from the first and second scales.

Further, the present method is easily adaptable to specimens having different (increased sizes). This facilitates the laboratory analysis of many different types and sizes of compacted specimens. Indeed, due to the sizes of aggregates used in recent mixtures, it is desirable to increase the size of the specimen undergoing evaluation, whether the specimen is prepared in the laboratory and/or extracted from the field. Typically, the size is increased from conventionally sized specimens having about a 100 mm (4 inch) diameter to specimens having about a 150 mm (6 inch) diameter for different thicknesses.

BRIEF DESCRIPTION OF THE DRAWINGS

The accompanying drawings, which are incorporated in and constitute a part of the specification, illustrate embodiments of the invention and, together with description, serve to explain principles of the invention.

FIG. 1 is a perspective view of a system for sealing a dense material specimen to inhibit liquid contacting the specimen during liquid displacement tests according to the present invention. The figure illustrates a porous material specimen in a resilient preformed bag positioned in a vacuum apparatus with an internal chamber and internal sealing means and controls for vacuum settings and exhaust speed adjustment according to a preferred embodiment of the present invention.

FIG. 2 is a side section view of the specimen in the preformed bag positioned in the apparatus of FIG. 1.

FIG. 3 is a side section view of an alternative embodiment of a vacuum apparatus and sealing means according to the present invention.

FIG. 21 is a tabular display of actual bag density determinations and core density calculations for a plurality of samples (including four different material types) which were sealed with the same vacuum setting (about 25 in Hg) according to the present invention.

FIG. 22 is a tabular display of a suitable data sheet for collecting and manipulating the raw data to establish core density according to the present invention.

DETAILED DESCRIPTION OF PREFERRED EMBODIMENTS OF THE INVENTION

Figures 4A, 4B, 4C:
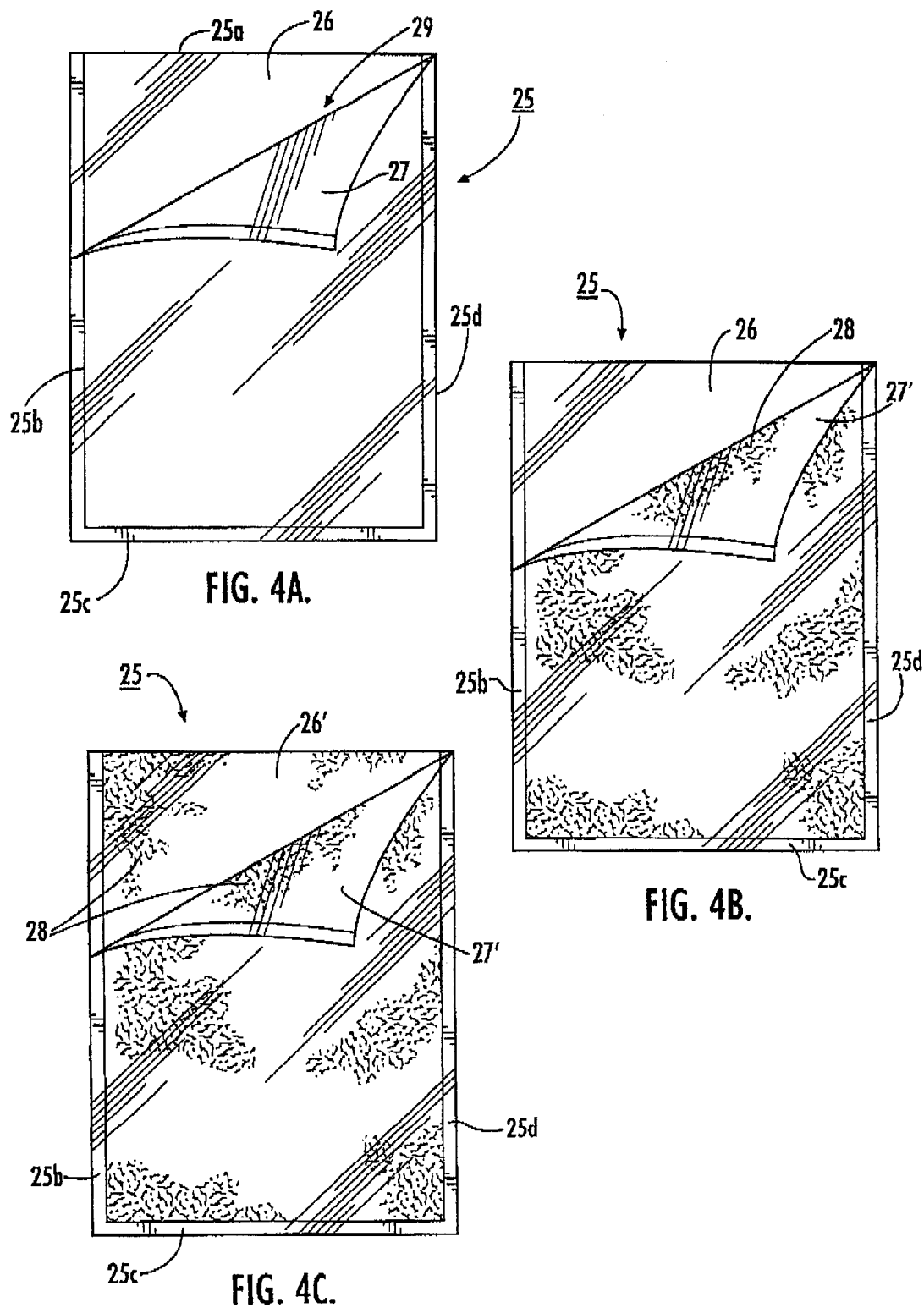
FIGS. 4A, 4B, and 4C are plan views illustrating preferred embodiments of preformed resilient bags according to the present invention.

The present invention will now be described more fully with reference to the accompanying drawings, in which preferred embodiments of the invention are shown. This invention may, however, be embodied in many different forms and should not be construed as limited to the embodiments set forth herein; rather, these embodiments are provided so the this disclosure will be thorough and complete, and will fully convey the scope of the invention to those skilled in the art. Like numbers refer to like elements throughout. In the drawings, layers or regions may be exaggerated for clarity.

Generally described, the present invention is directed to a method, system, apparatus, and water resistant jacket (which is preferably configured as a preformed bag) which acts to seal a porous sample from water infiltration in such a way that the sealing material is consistent over many samples and displaces a constant volume of liquid when used in liquid displacement tests, thereby improving the operator-reliant methods used at evaluation laboratories in the past. As used herein, the term "liquid" includes water, oils, aqueous mixtures, and preferably miscible blends thereof. In a preferred embodiment, the liquid displacement test is a water displacement test.

FIG. 1 illustrates a preferred embodiment of a system 10 for sealing a coarse porous material specimen in preparation for liquid displacement tests according to the present invention. As shown, the system 10 comprises a vacuum apparatus 12 with an internal (encloseable) vacuum chamber 13 having corresponding upper and lower and recesses 13a, 13b. The vacuum chamber 13 includes an upper lid 14 and a base 15, the upper recess 13a being formed in the lid 14 and the lower recess 13b being formed in the base 15. The upper and lower recesses 13a, 13b are sized and configured to receive a material specimen 20 positioned in a preformed bag 25 therein. In operation, the lid 14 is operably associated with a hinging portion 17 and pivots about the base 15 and closes to contact the base 15 and enclose the bag 25 and specimen 20 in the vacuum chamber 13. Preferably, as shown, the lid 14 includes a gasket 16 positioned around the rim to facilitate proper sealing of the apparatus 12 during use. Also as shown, the apparatus 12 includes a viewing port 30 which allows an operator to view the status of the contents during use.

As is also shown, the vacuum apparatus 12 also includes a vacuum pump 12a in fluid communication with a vacuum channel 12b which extends to an exhaust port 37. The exhaust port 37 is operably associated with an air channel 12c control rate adjustment means such as a valve 37a. The vacuum apparatus 12 also preferably includes a vacuum pressure adjustment 31, a timer adjustment 32 for the heater strip 36, an on/off switch 33, a stop button 34, and a gauge 38 to indicate the actual vacuum pressure in the chamber 13.

It is also preferred that system 10 include sealing means 35. As shown, in this embodiment, the vacuum apparatus 12 is configured with internal sealing means 35. In the illustrated embodiment, the sealing means 35 is shown as a heating element or strip 36 in alignment with two opposing bag clamps 36a, 36b. The sealing means 35 is mounted in the vacuum chamber 13 and includes the two opposing longitudinally extending clamps 36a, 36b which are configured to contact when the lid is closed over the base 15 and a heater strip 36. The internally mounted heater strip 36 can be incorporated into or positioned adjacent to one or both of the opposing heater clamps 36a, 36b. Alternatively, the heating and clamping means for sealing the edge portions of the bag 25 can be configured to extend around the perimeter of the bases 14 and 15 in a manner which allows the apparatus 12 to seal more than one side (or portion of one side) of the bag, such as two, three or even all sides of the bag, while the bag and specimen are held within the chamber 13 of the vacuum apparatus 12 (not shown).

As shown, in position, the front (open or unsealed portion) of the preformed bag 25 overhangs the surface of the lower clamp 36b. In operation, vacuum is pulled on the chamber 13 via vacuum pump 12a, vacuum channel 12b, and the exhaust port 37 until the vacuum chamber 13 reaches an appropriate vacuum level, or the air is evacuated or forced from the bag 25. The heater element 36 is preferably positioned in the bottom clamp 36b. After the vacuum reaches the appropriate level, the bottom clamp 36b is elevated and the heater element 36 activated. Thus, the clamps 36a, 36b exert a sealing force pinching against the opposing walls of the bag while the heater element is activated to securely seal the open edge portion of the bag while the bag 25 is held inside the vacuum apparatus 12 (i. e., prior to removal from the chamber 13). After the bag 25 is sealed, air is allowed into the chamber 13 through the exhaust port 37 which forces the sealed bag 25 to conform to the surface of the specimen 20. Preferably, the air enters through a restricted air channel 12c associated with the exhaust port 37. That is, the exhaust port 37 opening is controlled via valve 37a so as to control the rate of airflow into the chamber. This rate control helps control the force at which the bag walls conform to the specimen surface, thereby reducing the likelihood that the walls of the bag will puncture due to an abrupt return to atmospheric conditions attributed to an accelerated or uncontrolled exhaust rate or to forces associated with the re-introduction of air.

FIG. 2 illustrates the system 10 with the material specimen 20 and bag 25 positioned in the vacuum chamber 13 and the lid 14 with respect to the base 15. A suitable vacuum apparatus can be obtained from Ary Corporation, Kansas City, Mo. The commercially available apparatus is preferably modified to add vacuum and air exhaust controls according to the present invention.

In a preferred embodiment (not shown), the system 10 is configured such that a scale is integrated into the bottom base 15 of the vacuum apparatus 12 thereby allowing an automatic measure of the air weight of the specimen 25 to reduce the number of steps needed to be taken by an operator to establish the density of the specimen undergoing evaluation. This automatic weight measure can then be directed into a computer memory or computer program to allow easy semi-automatic computation of the density based on the input measurement parameters. Of course, the automatic input of the air weight can also reduce the separate listing of data needed to be input by laboratory operators thereby reducing operator clerical errors.

FIG. 3 illustrates an alternative (direct pull) system 10' with a vacuum apparatus 12' and a bag and specimen held external to the vacuum apparatus 12' during operation. The front portion of the bag 25 is positioned to overhang a portion of the vacuum chamber 13' while a major portion of the bag 25 is held external to the vacuum apparatus 12' during operation. The bag 25 may be held in position by a fixture or manually via lab personnel. In any event, in order to provide proper operation, the bag 25 is preferably held static while the vacuum apparatus 12' is engaged with the front edge of the bag. Indicia of depth may also be formed or positioned on the surfaces of the front portion of the bag 25 to help an operator positionally align the bag to a desired vacuum chamber entrance depth across the open edge of the bag to facilitate proper engagement (not shown).

As shown in FIG. 3, opposing upper and lower gaskets or seals 16' facilitate the sealing of the vacuum apparatus 12' when the lid and base 14', 15' are closed. In this embodiment, the sealing means is a laterally extending strip heater 36' which includes an upper clamping surface 36a' and a lower clamp support surface 36b' positioned in the apparatus 12' but mounted external to the vacuum chamber 13' (closer to or adjacent the receiving edge of the apparatus 12'). This heater arrangement allows the seal to be applied substantially contemporaneous with the vacuum to maintain the bag in its depressurized state, or in its surface collapsed or conformal shape (after the bag has been exposed to the desired pressure for the desired time but before the pressure or substantially immediately after the pressure has been removed). Preferred processing times and pressures will be discussed further below. A suitable vacuum apparatus can be obtained from Ary Corporation in Kansas City, Mo.

Other vacuum systems can be employed, such as for example, a direct connect or nozzle type vacuum system. In this embodiment, a vacuum pump and hose are in communication with a nozzle which is insertable into an opening formed in the bag 25 with the bag clamped securely therearound. Of course, the bag can be modified to configure the bag to accept the nozzle in manner which can facilitate the airtight seal between the nozzle and the bag during the vacuum step. For example, the open edge of the bag can be pre-sealed to along a major portion of the bag to provide a smaller opening to accept the nozzle during the air removal step. In operation, the nozzle directs the vacuum into the chamber of the bag and removes the air (not shown). Thus, similar to the externally held bag and specimen shown in FIG. 3, the direct-connect nozzle can be conveniently inserted into a bag to conform the bag to the shape of the specimen. An external sealing means can then be applied such as a manual sealing method or a sealing device such as is used in the commercial food preparation industry.

FIGS. 4A, 4B, and 4C illustrate preferred embodiments of a preformed resilient bag 25 according to the present invention. The preformed bag 25 includes two opposing walls 26, 27 which define the holding chamber 29 for the material specimen 20. Preferably, the preformed bag 25 is manufactured at a production facility remote from the laboratory or evaluation site such that it has three co-joined sides and a single open end when it is received at the evaluation site. The preformed configuration provides a ready-to-use bag 25 which the technician can employ with minimal preparation time at the laboratory test site.

Figure 14:
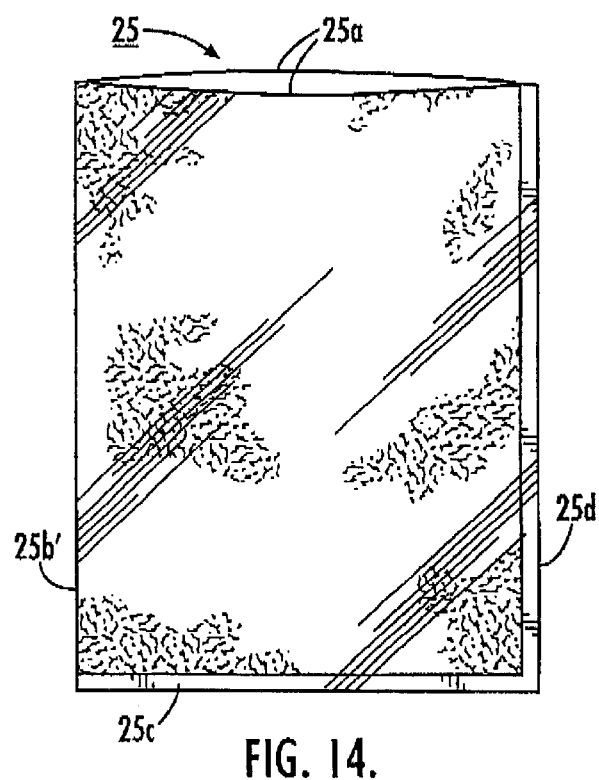
FIG. 14 is a top view illustrating a preformed bag having three co-joined sides, two of which are sealed together and one of which is provided by the unitary fold line of the material layer according to the present invention.
Figure 14A:
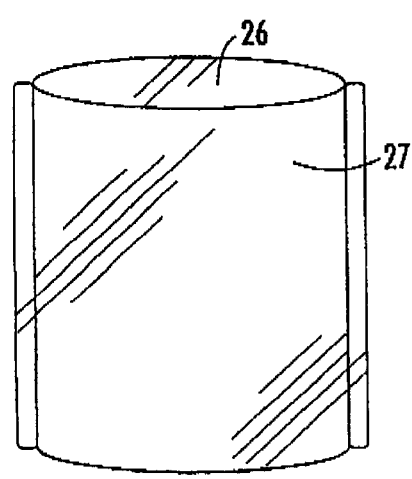
FIG. 14A is a perspective view of an alternate embodiment of a preformed bag having a preformed extruded bag forming a cylindrical bag where the two open ends can be joined at a laboratory evaluation use site.

FIGS. 4A–4C illustrate a preferred embodiment of a preformed bag 25 wherein the two opposing walls 26, 27 are co-joined on three sides by attaching the opposing sides 26, 27 at three corresponding sealing edges 25b, 25c, 25d. The three sides 25b, 25c, 25d thereby provide a continuous sealed edge perimeter. The fourth side 25a is left open so that a material specimen 20 can be inserted at the laboratory or use site (remote from the production site). FIG. 14 illustrates that the three co-joined sides 25b', 25c, 25d can be alternatively attached or formed. As shown, the first co-joined side 25b' is formed by a use of a folded unitary (single sheet of one or more material layers). Of course, the unitary portion of the bag (not requiring a sealed edge) can be alternatively configured on the bag such as on the end 25c opposing the open end 25a.

Figure 15A:
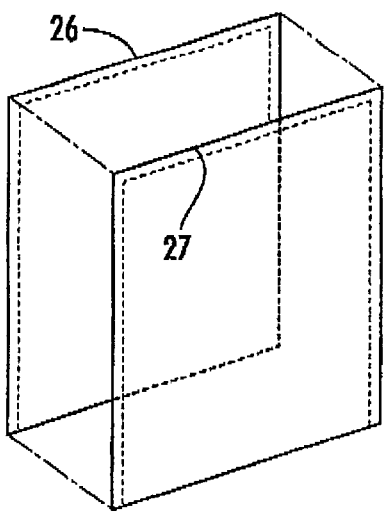
FIG. 15A is an exploded perspective view illustrating a resilient compressible bag which is formed by overlaying and sealing two pieces of material around the perimeter according to the present invention.
Figure 15B:
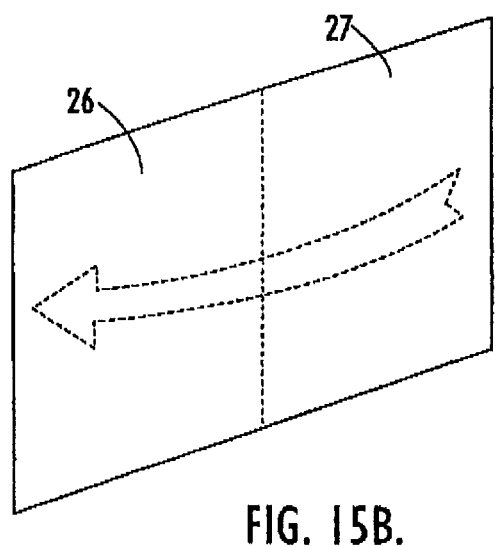
FIG. 15B is a perspective view of a unitary material bag according to the present invention illustrating fold lines therefor.

Alternatively, the "preformed bag" 25 of the present invention can be provided as a preformed bag structure which is joined along less than three sides 25b, 25c, 25d at a remote production site, such as along one or two sides, and still minimize the amount of trimming or even prevent the step of material trimming at the evaluation site at all. When two sides are joined, preferably two opposing sides such as those shown by sides 25b, 25d, the preformed bag 25 structure provides a "bag core" with a chamber 29 which can allow the technician to assemble the specimen 20 into the chamber 29 of the water jacket with the addition of one or two more supplemental or "side" sealing steps at the evaluation site, but still without requiring the operator to trim off unknown amounts of material and undesirably potentially degrading the reliability of the test results. FIGS. 15A and 15B illustrate two preferred fabrication configurations. FIG. 15A illustrates two separate sheets of material with one or more sides sealed at a production site. FIG. 15B illustrates a unitary pre-cut material sheet which can be folded along the fold lines to define one co-joined side (shown in dotted lines) and preferably sealed along the other two edges at a production site.

Figure 15C:
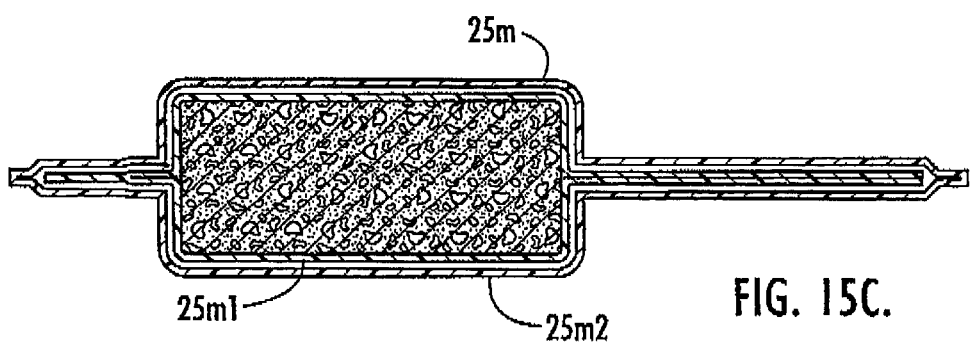
FIG. 15C is side section view of a specimen sealed in a multi-bag embodiment according to the present invention.

FIG. 15C illustrates a multi-bag embodiment 25m of a water jacket according to the present invention. As shown, the specimen is held inside a first bag 25m1 which is positioned within an outer second bag 25m2. The first bag 25m1 can be formed of a different material than the second bag 25m2. Preferably, the inner or first bag 25m1 is formed of a durable resilient material to resist punctures as it conforms to and rests against the exterior contours of the specimen 20. It is also preferred that the first bag 25m1 be sized and configured to be enclosed within the second bag 25m2. The first bag 25m1 does not need to be separately sealed or indeed, as shown, sealed at all.

In one embodiment, as illustrated in FIG. 4B, at least one of the inner surfaces of the two opposing walls 26, 27' includes a series of air channels 28 formed thereon. Preferably, the air channels 28 are coextensive with one of the walls 26, 27'. The air channels 28 are configured such that air can more easily escape from the bag as the chamber 29 deflates to rest against the exterior surface of the internally held specimen 20 and thus facilitate the surface conformal collapse of the bag against the exterior surface of the specimen (FIG. 9D). FIG. 4C illustrates that the air channels 28 can be formed onto the inner surface of both walls 26', 27'. Air channels 28 can be formed in a number of suitable configurations and are preferably configured to interconnect to the open edge portion of the bag 25. It is preferred that bags 25 with air channels 28 be used with the externally held bags used with direct pull vacuum equipment such as that shown in FIG. 3 while the bags 25 which are free of air channels 28 (such as those shown in FIGS. 4A, 5A, and 6A) be used with the vacuum apparatus of FIG. 1. Bags 25 of either type may be used with direct connect or nozzle type vacuum systems as described above.

In a preferred embodiment, the material specimen 20 is a porous compacted material specimen typically having interconnecting voids such as a compacted soil, concrete, aggregate, and bituminous samples. As such, the density measurement methods of the present invention are preferably used to analyze compacted material specimens which comprise, either alone or in combination, one or more of compacted soil, concrete, aggregate (loose and/or compacted), and compacted asphalt and/or bituminous material samples. Typically, the compacted material specimen 20 is a cylindrically extending dense core extracted from a roadway pavement or molded in a laboratory with mixed material samples representative of materials used in the field and, as such, this type of core includes a rough or coarse exterior surface. Of course, the specimen is not limited thereto as discussed above. Further, the material specimen 20 can be an aluminum block which typically has a smooth surface and a known density. As such, the aluminum block can act as a standard reference and can be used to determine the standard density for each type or size bag 25. Of course, other solid materials and configurations can also be used to provide the known standard reference.

Preferably, the compacted material specimen 20 has a four or six inch width or diameter and is on the order of from about 1–6 inches thick. Because, the compacted material specimens 20 are typically formed in standardized sizes, a set of bag 25 sizes can be conveniently be provided to allow a technician to select one from a collection of several preformed sizes. The particular bag selected is configured and sized to contain the particular size (or a range of sizes including that size) material specimen 20 and/or porosity or coarseness of the specimen undergoing analysis.

Preferably, the diameter of the cylindrically molded or field obtained specimens 20 (or length of sawed specimens) is at least equal to about four times the maximum size of the aggregate used therein. It is also preferred that the thickness of the specimen 20 is at least one and one half times the maximum size of the aggregate used therein. For example, for many roadway compacted mixtures, it is recommended that the specimen 20 be configured with about a 150 mm (6 inch diameter) specimen 20 having a thickness of at least about two inches.

For specimens having an exterior surface which is coarse, the preformed bag 25 is preferably configured to be puncture-resistant, as the bag 25 collapses to contact and conforms to the exterior surface of the material specimen during the sealing operation. A preferred embodiment of the present invention is therefore a puncture-resistant bag which is conformable to the exterior surface of the specimen. The puncture resistance can be provided by one or more of, material selection (type, size, and thickness), use of multiple layers of materials, use of multiple numbers of bags, and the use of reinforcement patches in areas of high-contact force. Preferably, the puncture resistance is also provided by a method which controls the rate of exhaust into and and/or evacuation out of the vacuum chamber 13 at the exhaust port 37 in a manner which is sufficient to slow the abrupt introduction of air back into the chamber 13 after sealing.

Figure 5A:
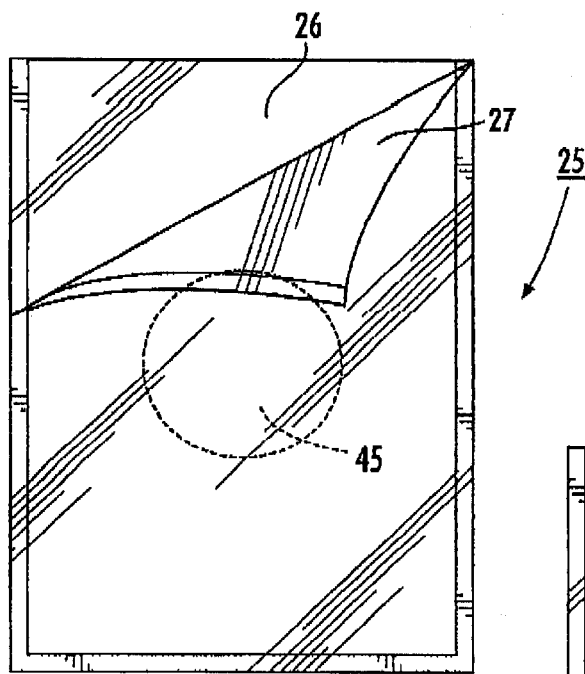
FIGS. 5A, 5B, and 5C are plan views illustrating the preformed resilient bags of FIGS. 4A, 4B, and 4C with integral reinforcement patches according to the present invention.
Figure 5B:
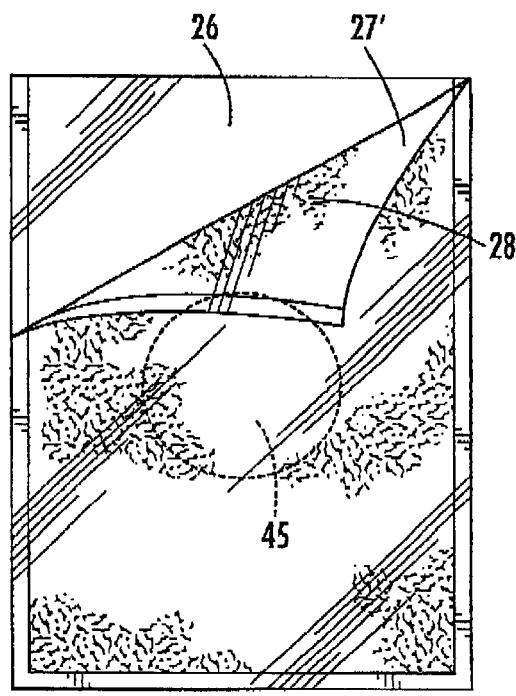
Figure 5C:
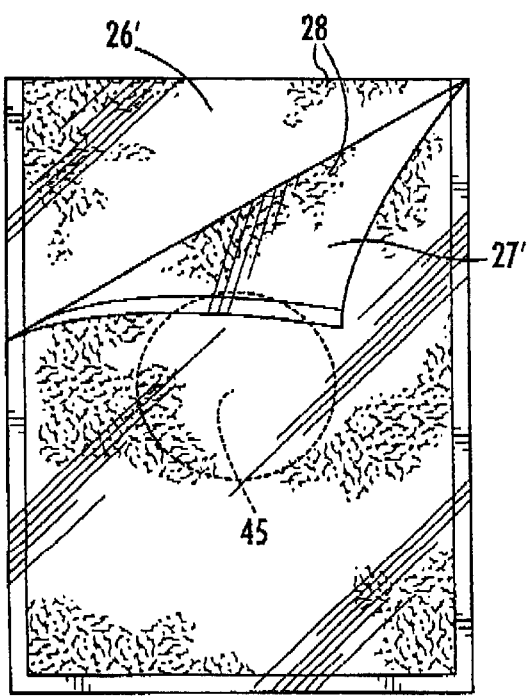

FIGS. 5A, 5B, and 5C illustrate preformed bags 25' with at least one integral reinforcement patch 45. Preferably, the reinforcement patches 45 are formed onto opposing internal surfaces of the first and second walls 26, 27. It is further preferred that the reinforcement patch 45 is configured to correspond to the shape of the upper or lower surface of the material specimen. Inasmuch as many of the bituminous material specimens used in construction are cylindrical, it is preferred that for this application, the reinforcement patch 45 be configured substantially as a circle and positioned on the bag 25 such that it overlies the specimen when the material specimen 20 is positioned therein. Of course, the reinforcement patch configuration will preferably correspond to the particular specimen undergoing analysis. In addition, other configurations side reinforcement patches may also be used and are preferably sized to correspond with the thickness and shape of the sides of the particular specimen undergoing analysis.

Figures 6A, 6B, 6C:
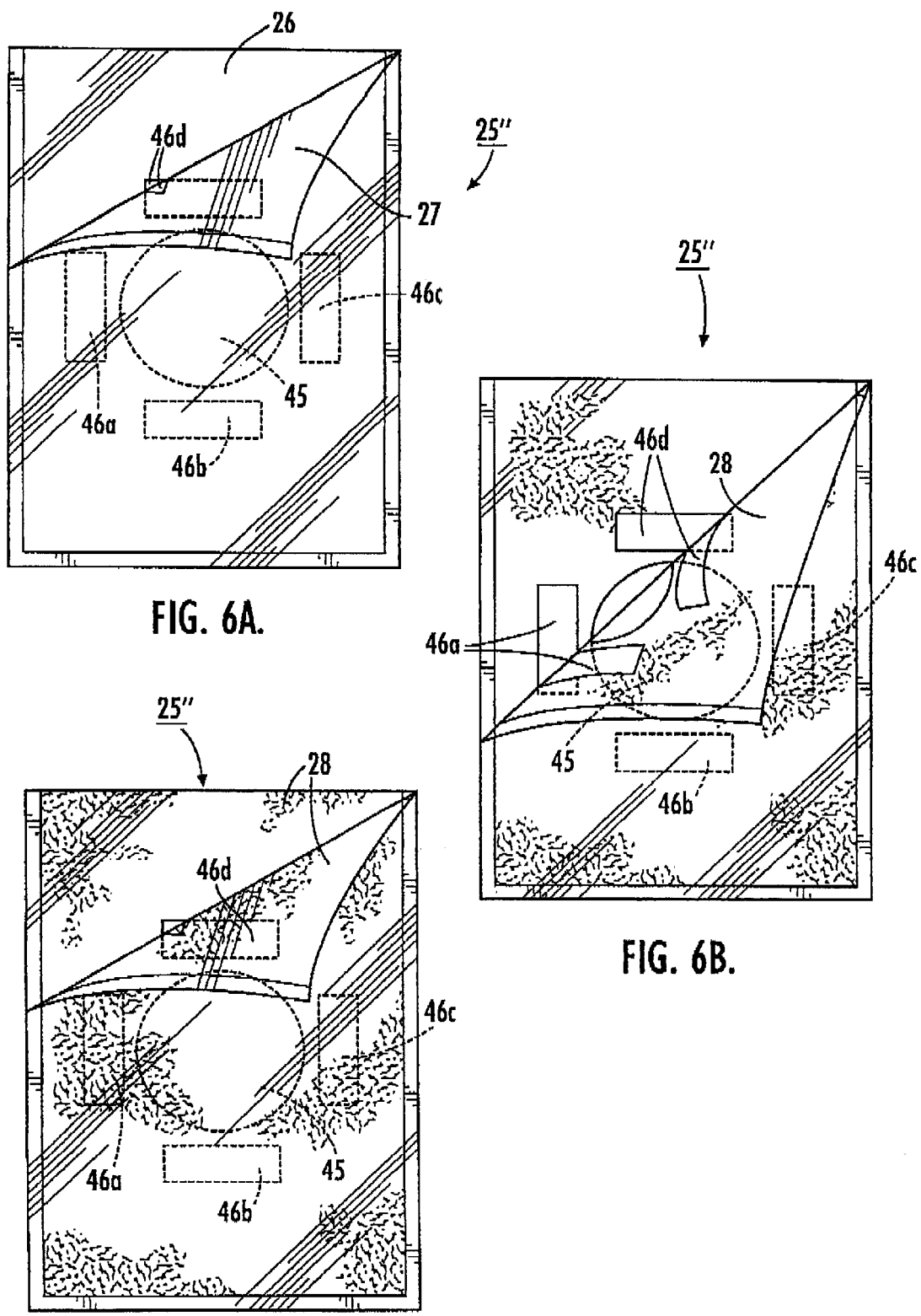
FIGS. 6A, 6B, and 6C are plan views illustrating additional embodiments of integral reinforcement patches according to the present invention.

FIGS. 6A, 6B, and 6C illustrate preformed bags 25"with alternate embodiments of integral reinforcement patches according to the present invention. As shown, the preformed bags 25" include at least one wall of the bag 26, 27 with a centrally positioned circular patch 45 and a plurality of peripheral reinforcement patches 46a, 46b, 46c, 46d on or formed into the bag to provide additional strength in predetermined regions of the preformed bag 25". Preferably, the peripheral reinforcement patches 46a, 46b, 46c, 46d, are positioned on the walls of the bag 26, 27 such that they fold over a portion of the sides of the specimen 20 as the bag 25 collapses to conform to the exterior shape of the specimen (FIG. 9D). Of course, other reinforcement patch configurations can also be employed within the scope of the present invention and the present invention is not intended to be limited to the exemplary reinforcement configurations shown herein. For example, circular patches can be applied to the top and bottom of the specimen and also applying cylindrical or linear wrapped patches onto the specimen to wrap around the sidewalls of the specimen. In this example, substantially all of the exterior surfaces can have reinforcement patches applied before sealing in the bag.

Figure 7:
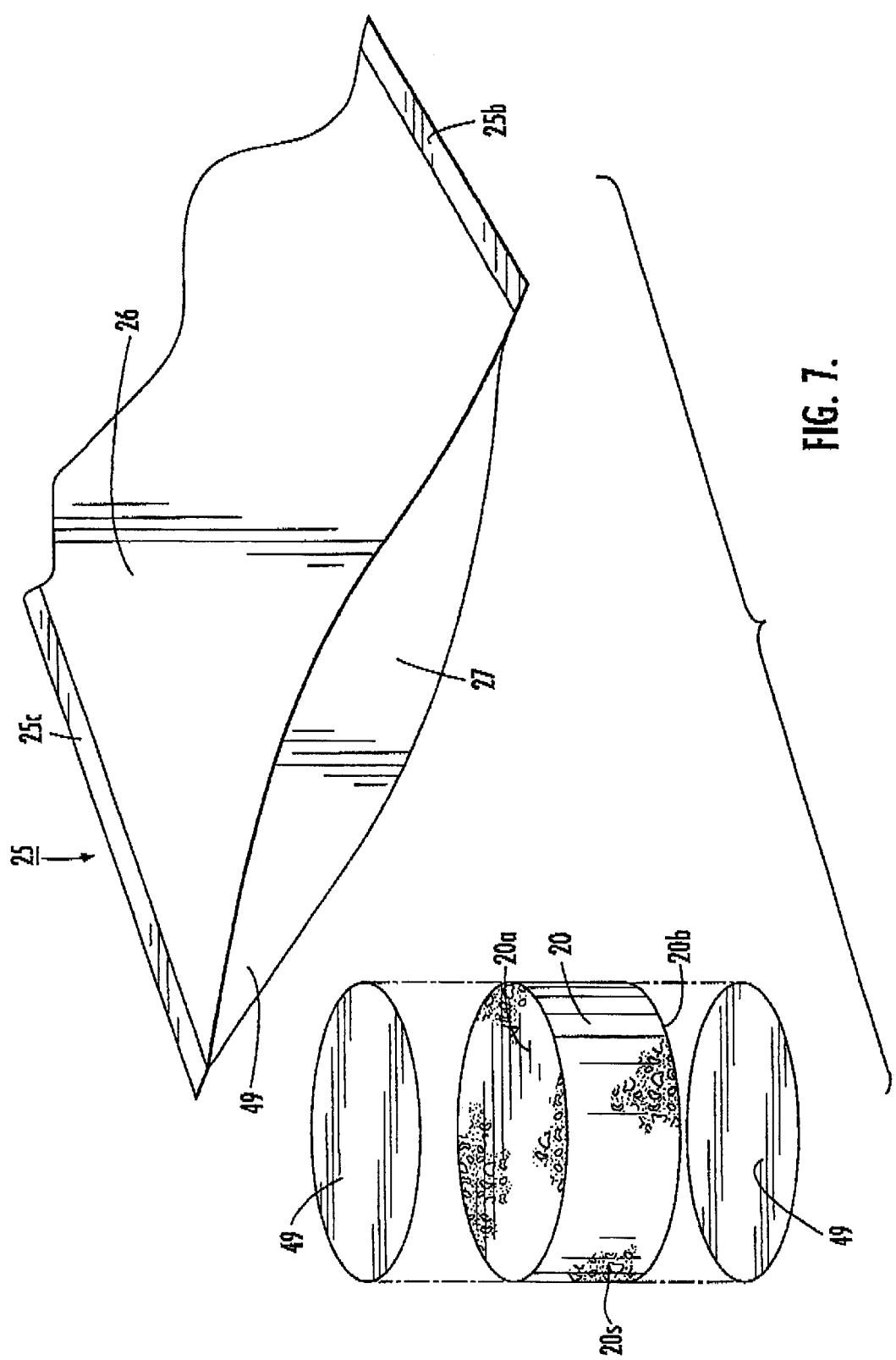
FIG. 7 is a partial exploded perspective view illustrating supplemental reinforcement patches positioned over a specimen prior to insertion into a preformed bag according to another embodiment of the present invention.

FIG. 7 illustrates an alternate embodiment of supplemental reinforcement patches 49. As shown, these supplemental reinforcement patches 49 are substantially flat circular patches which are positioned onto the top and bottom exterior surfaces 20a, 20b of the specimen 20 itself before the specimen 20 is inserted into the chamber 29 in the preformed bag 25. Of course, a single supplemental patch or portion of a patch can also be used for a corresponding selected single surface or portion of a single surface. In addition, small amounts of adhesive, or, preferably, a single-sided adhesive material can be used to attach to the surface of the specimen to hold the supplemental patch 49 in position during the insertion step. In operation, as the walls 26, 27 of the bag 25 collapse to contact the exposed coarse top and bottom surfaces 20a, 20b of the specimen, the supplemental reinforcement patches 49 act much like the integral reinforcement patches 45 to inhibit the puncture of the walls 26, 27 due to the contact with the coarse exterior surface. In addition, the supplemental reinforcement patches 49 can be configured to cover the sides and the top and/or bottom surfaces of the material specimen 20 and are preapplied to the specimen prior to insertion of the specimen 20 into the preformed bag 25.

Figure 9A:
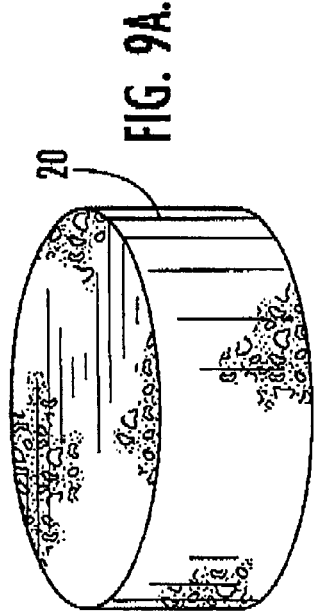
FIG. 9A is a perspective view of a porous specimen.
Figure 9B:
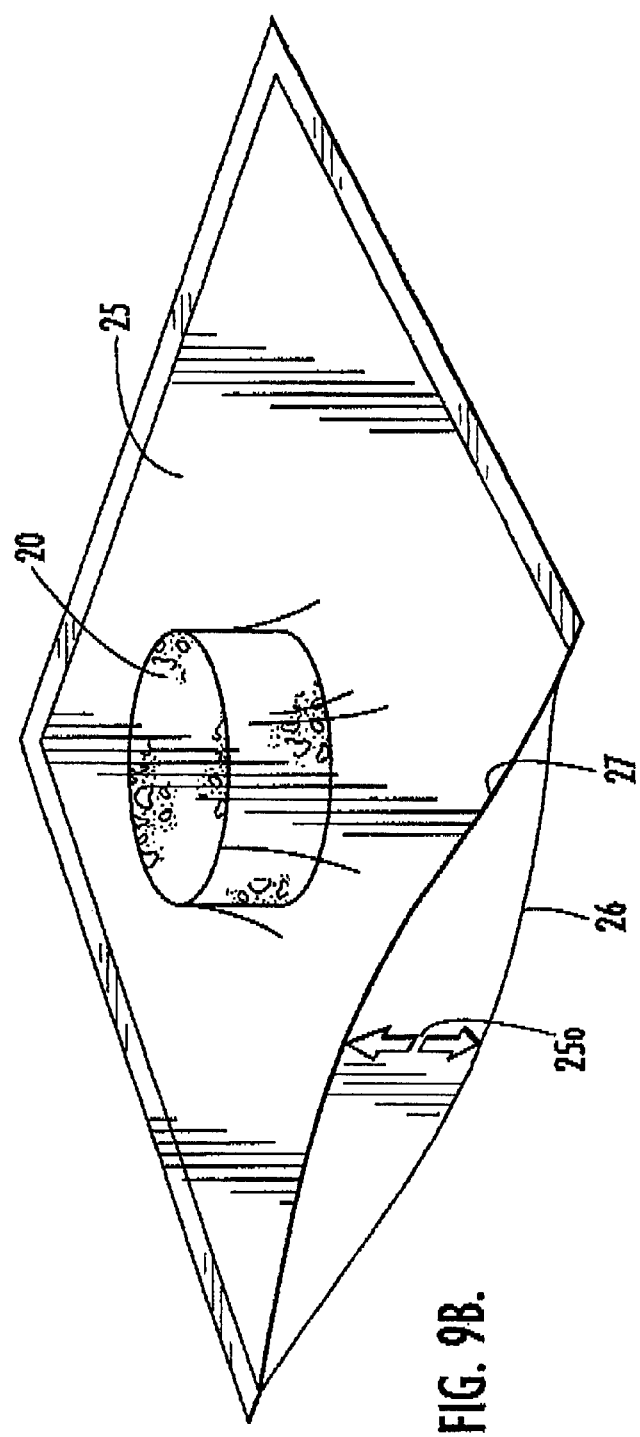
FIG. 9B is a perspective view of the porous specimen shown in FIG. 9A positioned in a preformed bag according to the present invention.
Figure 9C:
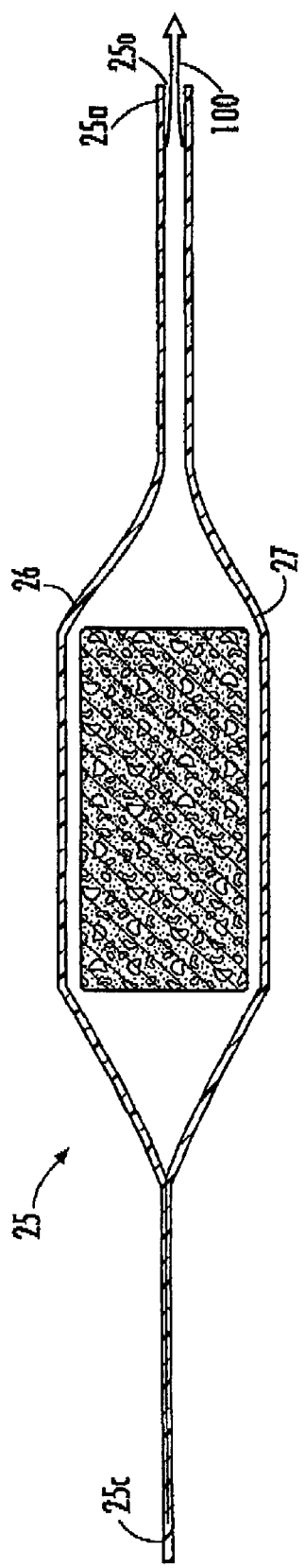
FIG. 9C is a side section view of the specimen and bag shown in FIG. 9B illustrating air being directed out of the bag opening.
Figure 9D:
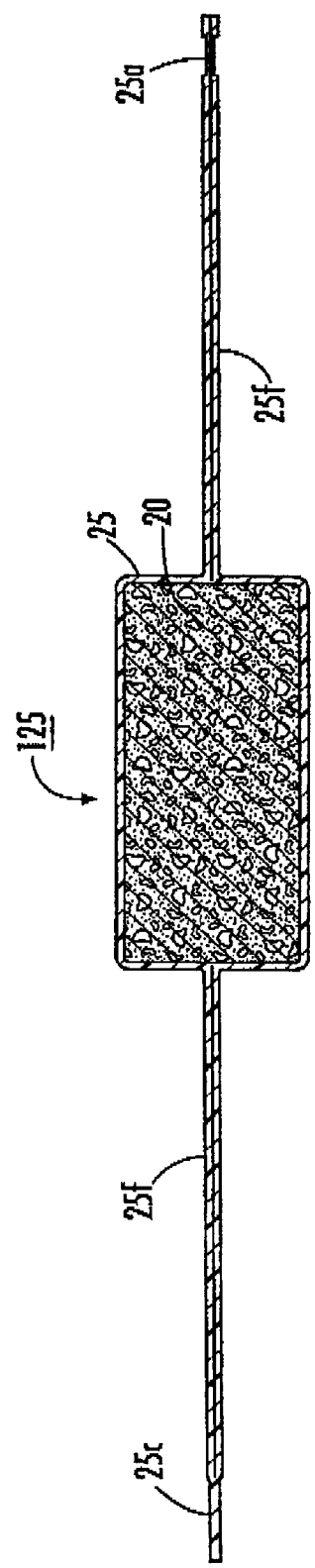
FIG. 9D is a side section view of the specimen and bag shown in FIG. 9B, illustrating the bag sealed such that the bag is collapsed to conform to the exterior of the specimen.
Figure 18:
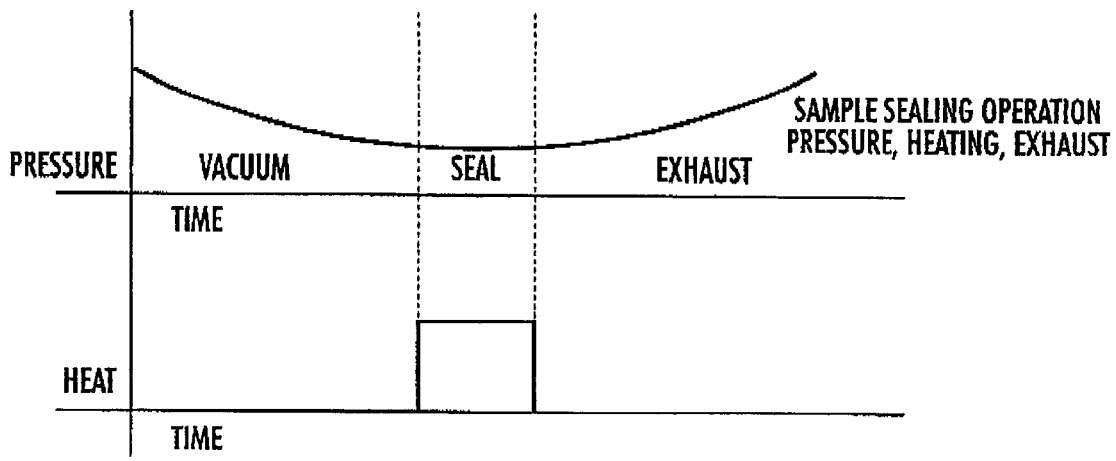
FIG. 18 is a timing chart of an apparatus with an integrated pressure and heating element control according to one embodiment of the present invention.

FIGS. 9A–9F schematically illustrate the sealing method of the present invention. FIG. 9A illustrates a specimen 20 which will be analyzed in a liquid displacement test. As shown in FIG. 9B, the specimen 20 is inserted into the preformed bag 25 having one opening 25o formed therein. Preferably, as shown, the opening 25o is defined by an non-joined segment or side of overlaying first and second walls 26, 27. As shown in FIG. 9C, the bag 25 is configured to define a fluid (i.e., gas) exit path 100 through the opening 25o responsive to a decrease in pressure. This decrease in pressure can be provided in several ways, such as by positioning a vacuum or pressure source in fluid communication with the fluid exit path 100 or the outside of the bag providing a pressure differential thereacross. When used with the vacuum apparatus 12 of FIG. 1, the bag is positioned in the chamber 13 such that the opening 25o of the bag extends across the sealing element 36. The vacuum pressure is selected (preferably automatically or semi-automatically as will be discussed further below), the sealing time is indicated (with a vacuum response delay time), the lid 14 is closed, and the vacuum apparatus 12 is activated via on/off switch 33. Once the pressure in the vacuum chamber 13 has reached the desired level, the heating element 36 is activated and the mouth or opening of the bag 25o is sealed. Air is then allowed to enter the chamber 13 at a controlled rate which causes the collapse of the bag against the sealed specimen. FIG. 18 illustrates a preferred pressure timing chart (evacuation, seal, and exhaust) according to the present invention. Preferably the exhaust time is greater than about 30 seconds, and more preferably about 35 seconds.

After the lid 14 is opened or, preferably, during the controlled exhaust introduction, the vacuum chamber is exposed to atmospheric or ambient pressure producing, as shown in FIG. 9D, substantially surface conformal bag-sealed specimen 125. The bag-sealed specimen is easy to handle, puncture resistant, and is configured to inhibit water from affecting the specific gravity measurements for porous samples. In operation, the air pressure forces the bag 25 to conform or press against the exterior contour or surface of the specimen, i.e., collapses the bag against the top and bottom surfaces as well as sides 20a, 20b, 20s. Also as shown, the method of the instant invention also preferably causes portions of the first and second walls 26, 27 to align and collapse to produce flat end portions 25f away from the specimen 20. This repeatable configuration advantageously allows the sealing method to yield a water jacket for a plurality of specimens in a manner which provides a substantially constant water displacement volume irrespective of operator material application (trimming, stretching and the like). It will be appreciated that removing the air (substantially all) from the bag prior to sealing is preferred while simply pressing the material layers 26, 27 together is not preferred.

Figure 9E:
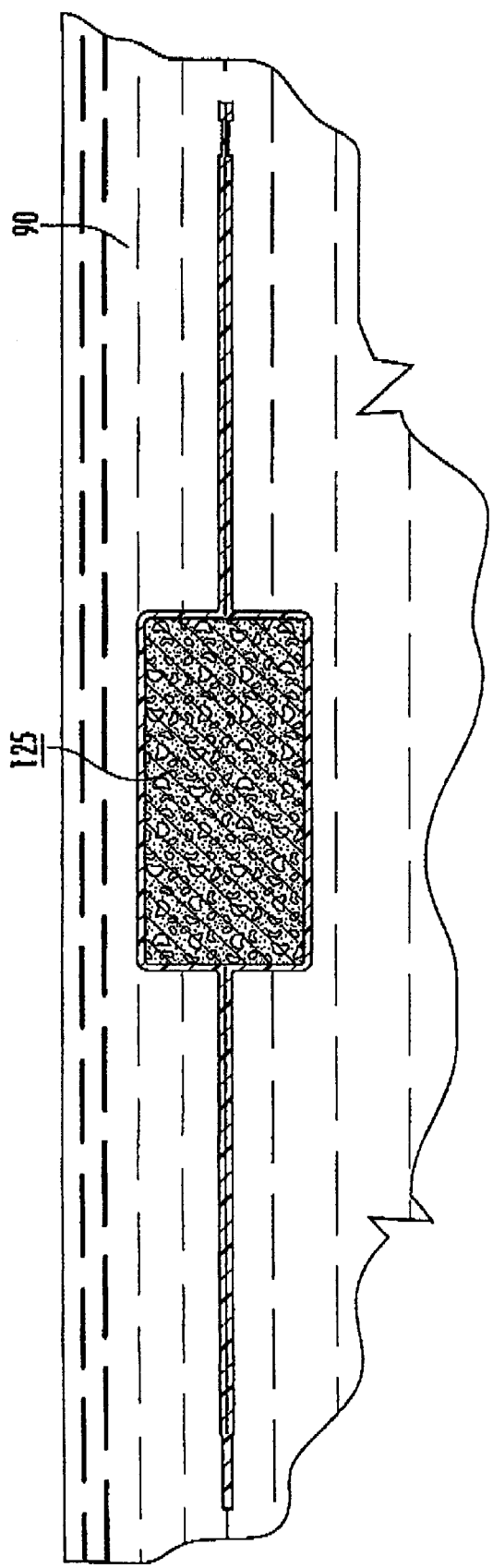
FIG. 9E is a side section view of the sealed specimen of FIG. 9D illustrating its use in a water bath for a water displacement evaluation.
Figure 9F:
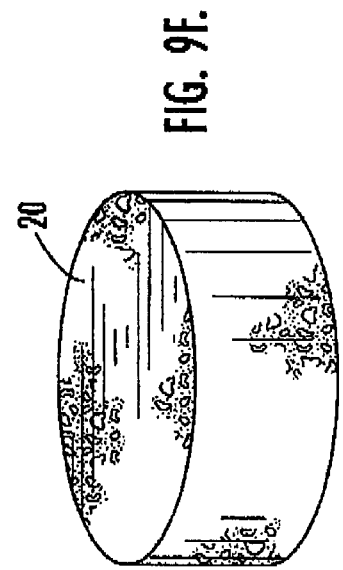
FIG. 9F is a perspective view of a porous specimen subsequent to the water bath step shown in FIG. 9E, illustrating that after removing the specimen from the sealed bag, the specimen's material composition and structure are intact.

FIG. 9E illustrates the sealed specimen 125 is positioned in a water bath 90 for water displacement test evaluation. The bulk specific gravity or density of dense porous specimens by water displacement calculations can now be reliably determined. FIG. 9F illustrates that the specimen remains structurally intact after the bag is removed (simply by destroying the seal and removing the specimen from the bag). Advantageously, this specimen can still undergo additional evaluation.

Preferably, in operation, the vacuum apparatus 10, 10' is preset to operate at predetermined vacuum pressures and times corresponding to the particular specimen type undergoing sealing as well as the type of bag being used therewith. For example, the apparatus 10, 10' can be configured to receive operator input information regarding one or more of the size, configuration, density, and material composition of the specimen as well as the type of preformed bag (usually a product identification number will suffice as it will define the material type, dimensions, standard density correction factor, etc). Typically, the specimens 20 evaluated or processed in a laboratory are presented in one of several standard configurations and material mixtures; allowing advance pressure operational parameters to be predetermined and pre-programmed for automatic operation at the laboratory site. It is expected that a standard vacuum setting will be acceptable for use in the methods of the present invention across a wide range of material specimens including specimens with different thicknesses and textures. The vacuum setting may need to be periodically adjusted for optimum performance so as to account for equipment drift such as may occur over time with the age and use of the vacuum pump.

Preferred vacuum pressures used to conform the bag 20 to the specimen's exterior surface contour can depend on the particular specimen 20. However, it has been found that a single vacuum pressure and/or controlled exhaust rate can be suitable for a number of specimen types and sizes for a particular bag. One preferred bag is a polymer material (preferably a polyolefin) produced by a metallocene catalyzed reaction. In another preferred embodiment, the bag material is formed of polyethylene which includes at least about 20% nylon (this polyethylene/nylon combination is known in certain circles as "polynylon"). Dimensionally, for relatively large specimens, preferred embodiments configure the wall thickness at about a 6.0 mil thickness and a bag width×length of about 16×16 inches or 10×16 inches. A preferred vacuum setting is a vacuum which is above about 20 in Hg, and more preferably, at or above 25 in Hg, and, even more preferably at or above 28 in Hg. Also preferably, the exhaust time (the time it takes to reach atmospheric conditions) is set at about at least 30 seconds, and more preferably, at about 35 seconds. These parameters have been confirmed as being suitable for compacted material specimens from the construction field, i.e., coarse, porous 6-inch diameter compacted bituminous cores. Indeed, this vacuum pressure is believed to be suitable for across many bag materials. The preferred vacuum calibration method can adjust the vacuum pressure and/or exhaust rate used to seal the compacted specimen 20 corresponding to one or more of the density of the bag (which can vary depending on the material type, thickness, and bag dimensions) and the type of material specimen 20 placed in the preformed bag. The vacuum pressure and evacuation, exhaust times may also vary depending on the material composition and thickness of the walls or number of layers and/or bags used to form the walls of the bag.

Figure 17:
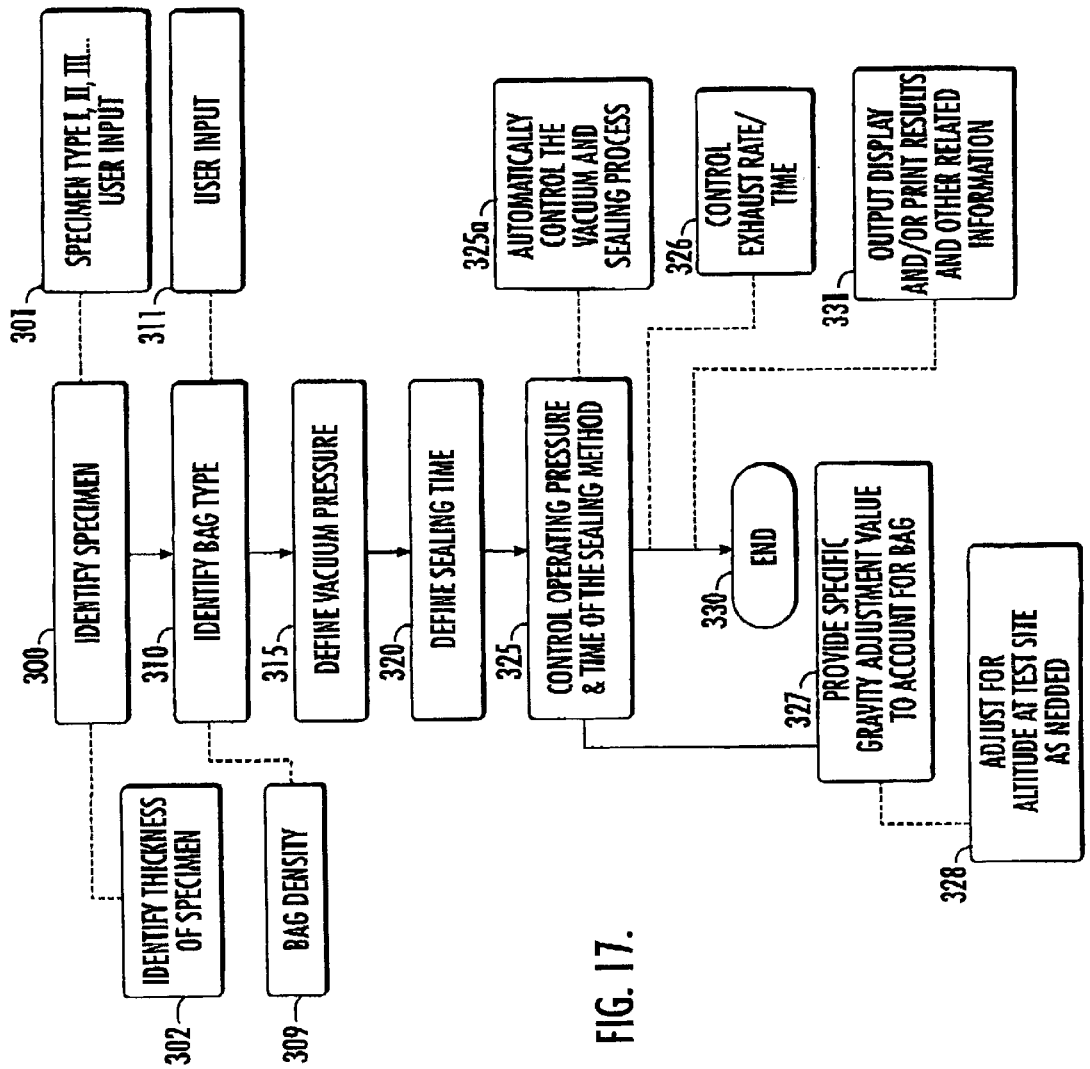
FIG. 17 is a flow chart of a method for sealing a material specimen which can reduce operator-induced variation on the sealed configuration according to the present invention.

FIG. 17 illustrates a flow chart of methods, apparatus (systems) and computer program products according to the invention. It will be understood that each block of the flowchart illustration, and combinations of blocks in the flowchart illustrations, can be implemented by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce computer implemented process such that the instructions which execute on the computer or other programmable apparatus provide steps for implementing the functions specified in the flowchart block or blocks.

Accordingly, blocks of the flowchart illustrations support combinations of means for performing the specified functions and program instruction means for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer instructions.

As shown in FIG. 17, the operator identifies the specimen undergoing evaluation and classifies it via predetermined criteria (Block 300). For example, the specimen can be classified by one or more of its surface roughness, size (width and/or thickness), configuration, material composition, or approximate composite or bulk density.

Figure 19:
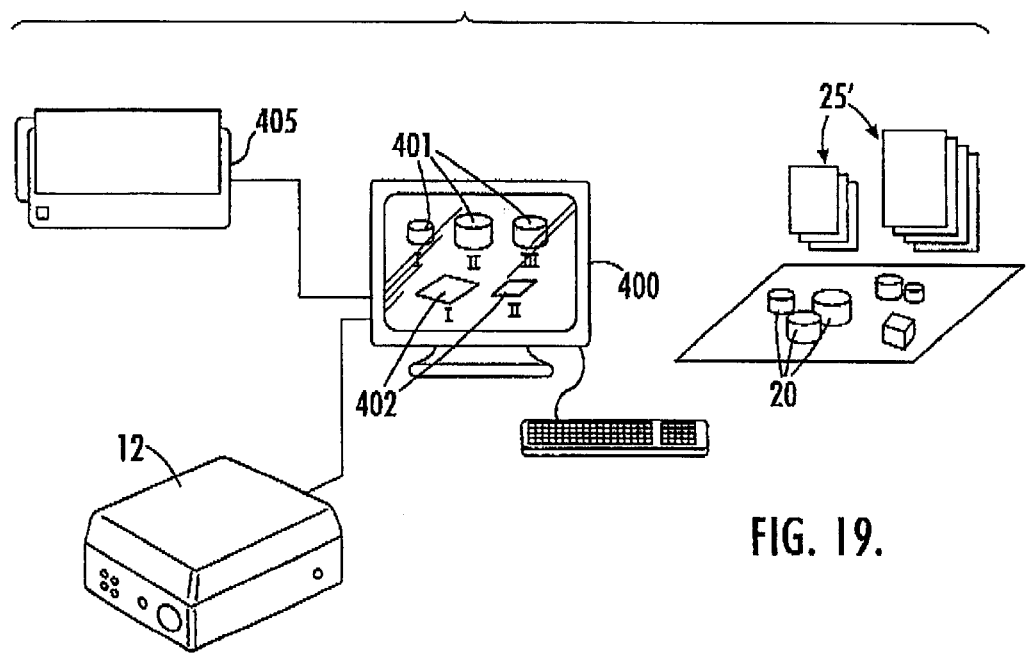
FIG. 19 is a schematic diagram illustrating a machine-controlled embodiment of a sealing system according to the present invention.

Preferably, the vacuum apparatus 12 is preferably operably associated with a computer control input (FIG. 19) which controls the operational vacuum of the vacuum pump 12a as well as the exhaust rate. Further, the computer has computer program code means which is configured to accept a user's input to let an operator select the specimen type having those identified criteria, i.e., specimen type I, II, III etc. (Block 301). Optionally, as shown in FIG. 19, a computer 400 operably associated with a vacuum apparatus 12 can be configured to display computer generated icons or digital pictures representing specimen types 401 in a manner which allows a user to easily select the specimen type 401 being sealed according to the present invention. Block 302 further illustrates that a user may input the thickness of the specimen independent of the core size (typically standardized cores with a 4 inch or 6 inch diameter in the construction industry). In any event, the operator selects the specimen type corresponding to the identified criteria. As is also shown in FIG. 19, the system or method preferably includes a printer 405 which automatically calculates the measurement results for the operator.

The operator can also identify the type of bag being used (Block 310). For example, the operator can identify or classify the preformed bag type according to predetermined evaluation criteria or product identification number which is associated with information such as one or more of its density (Block 309) size (dimensions, thickness), material, reinforcement patch configuration, air channels, or bag configuration. Alternatively, an operator can merely enter the product identification number which the computer program can associate with established manufacturing standards, i.e., bag type I, II, III or select it via a visual display of bag types 402 shown in FIG. 19. In any event as for the specimen identification, the method preferably allows user input of the bag type being used (Block 311). Because the preferred vacuum pressures and times are identified and pre-programmed corresponding to certain criteria such as one or more of the specimen thickness or type, or bag type or configuration, the computer program product can then proceed to calculate the optimum vacuum pressures and times for the particular procedure (Block 315). Indeed, in a preferred embodiment the operational pressures and times are automatically directed to the vacuum apparatus to automatically control the operational parameters of the apparatus, thereby minimizing the chance for operator error or variability.

Preferably, the method and/or computer program product is also configured to preset sealing or heating times to (semi) or automatically control the sealing step at the appropriate point and for the appropriate time during the pressure application and for a particular bag type thereby providing repeatability and consistency to the evaluation process (Block 325). It is also preferred (for chamber type vacuum systems such as shown in FIG. 1) that the method control the exhaust rate and/or time of the air (the entry of air back into the chamber) (Block 326). That is, for a particular type specimen 20 and bag 25, the method and automatic (or semi-automatic) operational control provides a sealed specimen 125 which will have substantially the same shape over a plurality of sealed specimens. The method then preferably provides the appropriate reference adjustment for the specific gravity determination (such as a calculated or measured bag density value) to offset the effect of the bag on the measurement (Block 327). Preferably, the method can adjust the bag reference adjustment value according to altitude variations which may be present at the test site (Block 328). Accordingly, the methods and bags of the instant invention thereby displace a constant water or liquid volume in the liquid displacement test to correspond with a known specific gravity adjustment value to minimize test variation attributed to the use of the bag to seal the specimen. Preferably, the test results are then output such as to a display monitor, or printer. The test results can include the test information for the specimen such as the specific gravity, porosity, density, sample type, bag type, date of test, and other pertinent information.

Figure 20:
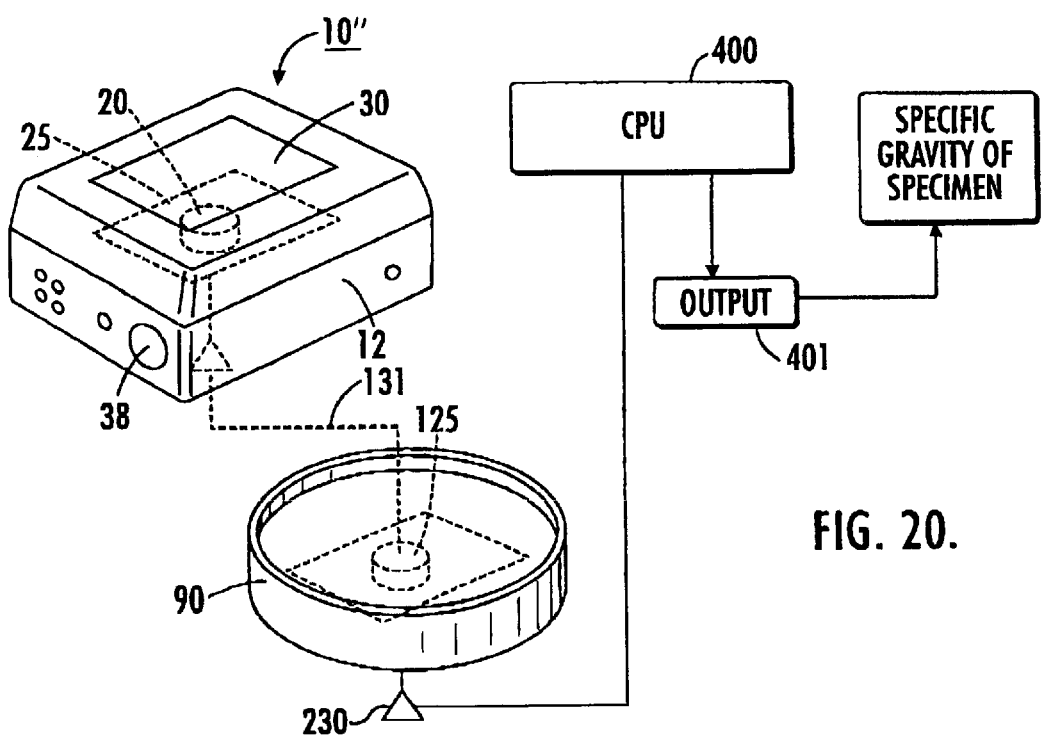
FIG. 20 is a schematic diagram of an additional embodiment of the present invention illustrating an integrated scale apparatus and feedback system configured to provide measurement data to a central processor unit to semi-automatically calculate the specific gravity of a material specimen.

FIG. 20 illustrates a preferred controlled substantially automatic measurement system according to another embodiment of the present invention. As discussed above, the vacuum system 10" preferably includes a scale 130 integrated into the interior of the chamber 13 to measure the weight in air (once the exhaust process has been completed such that the chamber is at ambient atmospheric conditions). This measurement is then relayed to a CPU such as a computer 400 which includes this value in the density calculations as discussed above. As also shown, it is also preferred that the water bath be operably associated with a scale 230 which is connected to the CPU 400. The direct input of this measurement can further automate the test procedure and reduce clerical errors. In one preferred embodiment, the scale 130 can be structurally associated with the water bath to provide a unitary scale used for both the vacuum measurement and the water bath measurement (indicated by dotted line 131). For example, a platform can be suspended from the scale into the water bath, the platform being configured to receive the sample and thus, automatically provide the measurement weight for this step into the CPU (not shown). As shown, the CPU can process the measurement data and calculate and output (401) the specific gravity or density of the specimen The output can be a printer, a display, and even an electronic message reporting the test result based on a coded serial number to a customer's desktop (providing faster test results).

In order to determine the adjustment factor for the bag, a test standard such as an aluminum calibration cylinder can be used. As is known to those of skill in the art, the specific gravity adjustment factor for the preformed bag 25 can be provided by determining the difference in liquid displacement for the aluminum cylinder alone and the aluminum cylinder sealed according to the present invention. The difference in the volume of water displaced is the volume attributed to the bag 25. Knowledge of the volume and weight of the porous specimen thus allows for calculation of the specific gravity of the porous sample. The initially determined displaced volume of the bag alone therefore provides a reliable adjustment factor to be applied to calculations used to determine the specific gravity of a plurality of specimens sealed according to the instant invention.

More particularly described, the specific gravity of the cylindrical aluminum calibration standard ($G_{al}$) at a predetermined temperature (25° C. +/−1° C.) is determined by first determining the mass in air and under water. The specific gravity is represented by the equation:

$$G_{al} = A_{al}/(A_{al} - B_{al}),$$

where $A_{al}$ is the dry mass of the aluminum cylinder in air (grams), and $B_{al}$ is the mass of aluminum under water (grams).

Next, the aluminum cylinder is dried and sealed in a preformed bag 25 as described herein. The volume of additional water displaced is determined. Of course, this process can be performed by sealing the aluminum in the bag, measuring the submerged weight of the aluminum and bag, and then removing the bag to submerge the aluminum alone to obtain the submerged weight attributed to the aluminum alone. In any event, during subsequent analysis, this established correction value (amount) is subtracted off the volume of each sealed specimen using similar preformed bag configurations or types leaving the water displacement value for the specimen alone.

Alternatively, the dry sealed mass of the cylinder and mass of the sealed cylinder under water is determined. The "apparent" specific gravity of the preformed bag 25 is determined at the 25° C. temperature by the equation:

$$\frac{D_{al} - A_{al}}{\left[D_{al} - E_{al} - \left(\frac{A_{al}}{G_{al}}\right)\right]}$$

where $D_{al}$ is the dry mass of the sealed specimen in grams, and $E_{al}$ is the mass of the sealed specimen under water in grams. The bulk specific gravity of the sealed specimen 125 of the instant invention can then be determined by the equation:
Bulk specific gravity is equal to:

$$\frac{A}{\left(D - E - \left(\frac{D-A}{F}\right)\right)}$$

where A is the weight of the dry specimen in air (grams), D is the weight of the dry, sealed specimen (grams), E is the weight of the sealed specimen under water (grams) and F is the "apparent" specific gravity of the preformed bag determined at 25° C. Thus, the density of the specimen can be calculated as the bulk specific gravity value multiplied by the density of water ($\gamma$) (or other liquid used) at 25° C.

In an alternate preferred embodiment, the actual density of the bag can be determined by measuring the bag's width, length and thickness to establish a bag volume and by obtaining the weight of the bag (such as via a scale) and then mathematically computing the bag density.

Figure 8:
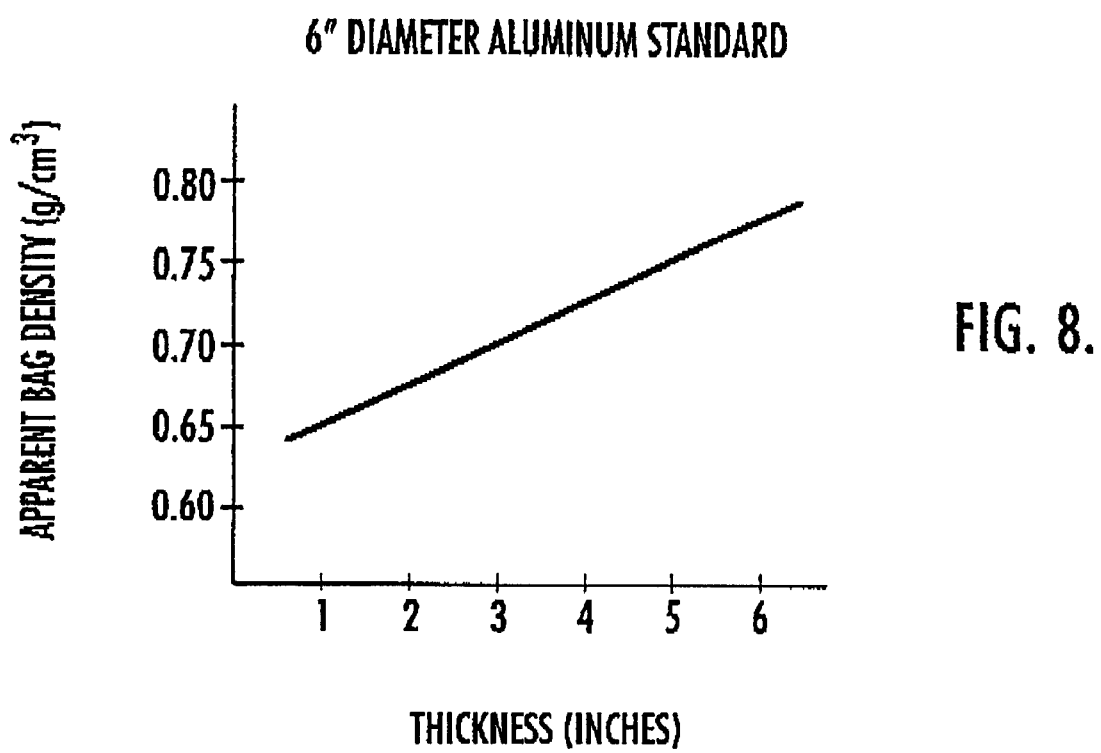
FIG. 8 is a graph of an exemplary relationship of apparent bag density versus thickness which can be used for determining the density of the preformed bag based on various different sizes of standard aluminum samples for a given vacuum operation time according to the present invention.

In a preferred embodiment, a relationship is established between the specific gravity of the preformed bag and a range of different aluminum standard reference block thicknesses for a given vacuum operation time. For example, the apparent specific gravity of the preformed bag 20 is determined for an aluminum reference block specimen having a diameter of 6 inches (150 mm) and thicknesses ranging from about 1–6 inches. A similar relationship can be established for other compacted material specimen sizes or configurations, such as for a 4 inch (100 mm) diameter core. These relationships can be graphically represented as shown in FIG. 8. Preferably, the apparent bag density versus specimen thickness relationship (i e., the calibration evaluation factor) for a plurality of different specimen configurations is predetermined at a first use point, or more preferably, at the original equipment manufacturer (OEM) which may display different mathematical models depending on the variables involved. Either way, the factory or first use calibration relationship model can eliminate the requirement for the laboratory technician to perform the aluminum standardization bag density test prior to each compacted material specimen 20 measurement. It is also preferred that the elevation of the test site be taken into consideration when establishing the calibration factors because the relationship can be affected by elevation when testing is performed. Further, it is preferred that the vacuum level and exhaust rate be set such that normal variations in elevation does not affect the density measurement. The bag density relationship for a compacted specimen across a range of specimen sizes can yield a reliable calibration factor which can be applied by a computer look up table or program to automatically adjust the calculation of the specimen density based upon the user input regarding the compacted material specimen 20 configuration under evaluation. Further, it is believed that the bag density relationship for a specimen size and thickness will be substantially independent of the type of material used to form the compacted material. compositions.

As discussed above, it is preferred that the bag be precision manufactured such that its dimensions and configuration are suitably controlled to minimize the variability in the bulk specific gravity and density determinations. As used herein, the term "high precision" or "precision" manufactured means producing the bags such that for a particular type, they have minimal variation across a statistically representative population. As such, it is preferred that the tolerances used to produce the bag be about at least +/−0.0002 inches in the thickness dimension and +/−0.1 inches in the other dimensions. Stated differently, it is preferred that the tolerances of the material thicknesses for each product type are predictably and reliably reproducible over mass production. It is also preferred that the bags be produced according to six sigma manufacturing standards to reduce process variation particularly in the thickness dimension.

Figure 10:
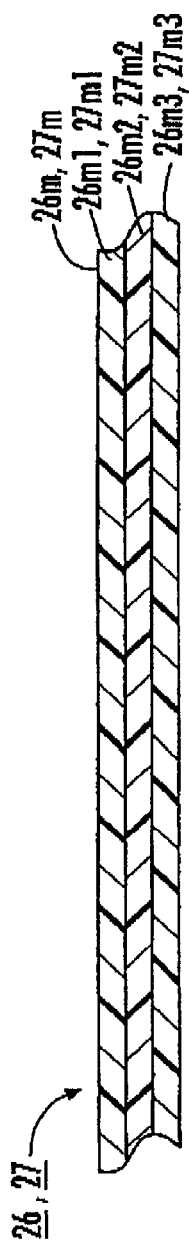
FIGS. 10 and 11 are enlarged partial section views of multi-layer walls for a bag according to the present invention.
Figure 11:
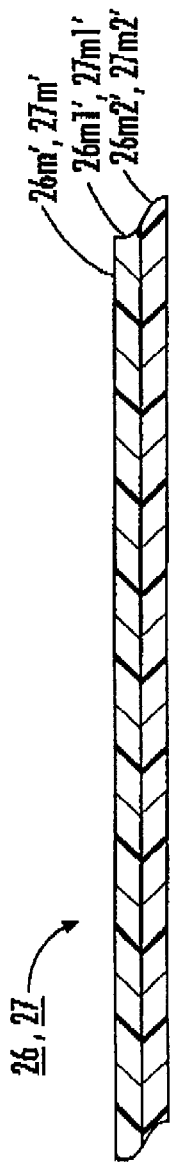
Figure 16A:
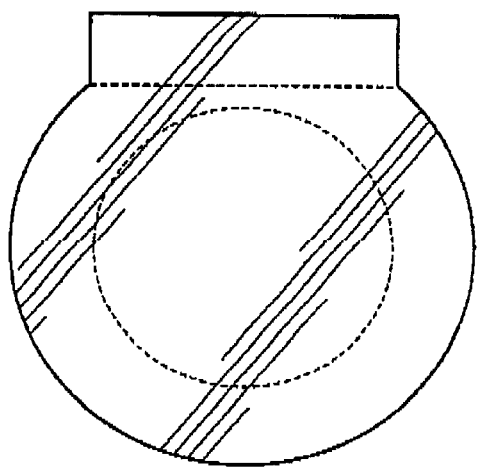
FIGS. 16A–16C are top views illustrating alternative configurations for the preformed bag according to the present invention.
Figure 16B:
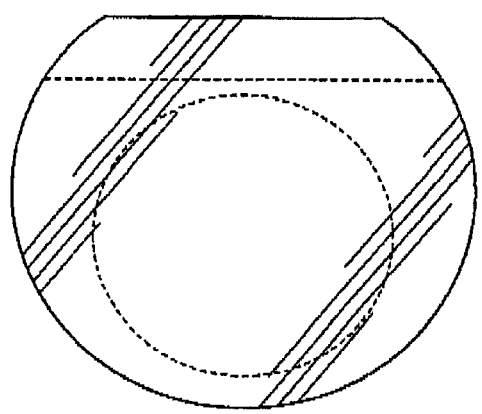
Figure 16C:
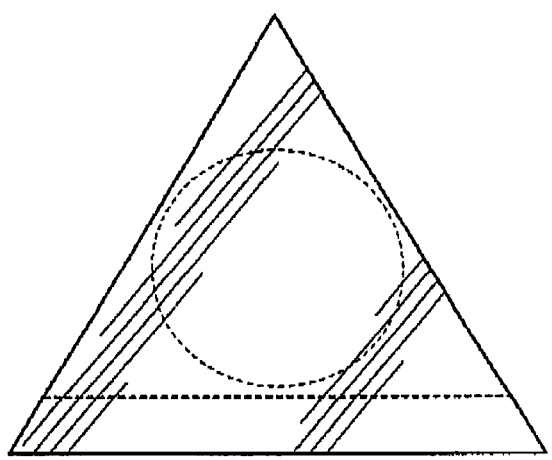

As shown by FIGS. 10 and 11, one or more walls 26, 27 of the bag can be formed of more than one layer of material. FIG. 10 illustrates a three-layer configuration 26*m*, 27*m* with three separate layers of material 26*m*1, 26*m*2, 26*m*3, and 27*m*1, 27*m*2, 27*m*3, respectively (the layers can be formed of the same material or materials which are different from each other). FIG. 11 illustrates a dual layer configuration 26*m*', 27*m*' with layers 26*m*1', 26*m*2', and 27*m*1', 27*m*2'. The multi-layer configurations 26*m*, 26*m*', 27*m*, 27*m*' can be used in lieu of or in addition to the reinforcement patches 45, 49 described above. Although illustrated for clarity throughout as a rectangular shaped bag, the present invention is not limited thereto. Indeed, many additional shapes and configurations can be employed according to the present invention. For example, but not limited thereto, FIGS. 16A, 16B, and 16C illustrate additional shapes or configurations of a preformed bag 225, 225', 225'', respectively.

In sealing coarse construction type compacted material specimens 20, the bag selected to seal the specimen is preferably selected to meet two functional parameters. More particularly, the material used for the bag is preferably selected such that it is sufficiently strong and/or durable to be puncture resistant and also sufficiently flexible to conform to the irregular contours of the surface of the coarse specimen when processed as described herein. As discussed above, during the sealing process, the walls of the bag collapse to substantially conform to the exterior of the specimen 20. This easy conformation with the contours of the specimen will provide a predictable repeatable sealed shape which, in turn, allows for a constant water volume displacement and a constant reliable adjustment factor for the specific gravity analysis.

It is also preferred that the bag 25 be configured with respect to the material specimen 20 undergoing evaluation such that width of the bag 25 (i.e., the opening along one side) is about at least twice the diameter or width of the compacted material specimen 20. It is additionally preferred that the maximum width of the bag be less than about three times the diameter or width of the compacted material specimen 20 to reduce excess amounts of sealant (bag) material which can potentially result in measurement inaccuracies attributed to one or more of air bubbles being trapped by the additional material or stretching that can occur during vacuum operation which can result in short term drift in weight measurements during water displacement evaluations.

It is also preferred that the size of the bag be configured such that it closely corresponds to the size of the specimen undergoing evaluation to reduce the amount of excess material employed and thereby reduce the potential for entrapping residual air therein.

Suitable bag materials include, but are not limited to, elastomeric and plastic materials and polymers. For the purposes of the inventions herein, the term "polymer" to be broadly construed to include homopolymers, copolymers, terpolymers and the like. Similarly, the terms "blends and mixtures thereof" include both immiscible and miscible blends and mixtures. Examples of suitable materials include, but are not limited to, polyoelfins (e.g., polyethylenes, polypropylenes), polystyrenes, polymethacrylates, polyvinyls, polydienes, polyesters, polycarbonates, polyamides, polyimides, polynitriles, cellulose, Tyvak® and cellulose derivatives and blends and mixtures thereof. Two preferred bag materials are noted above.

FIG. 21 is a table of measured parameters according to the present invention. The top portion of FIG. 21 provides data associated with two standard aluminum with known densities. The bag densities determined from this portion of the test were averaged for subsequent determination of the density of the asphalt core samples given in the lower portion of the table. The lower portion of the table is a listing of results or calculations and measurements used to determine core density according to the present invention.

FIG. 22 is a sample of a data intake sheet suitable for determining core density of a compacted specimen according to the instant invention. As shown, each column has an "alpha" identifier which in subsequent blocks may be mathematically manipulated with other values to finally provide the core density (identified as "p"-block-or Col. "p" of the bottom table) or bag density (identified as Col. "I", top table). Accordingly, FIG. 22 illustrates a preferred computational method and method steps for determining core densities and/or the bag densities according to the present invention.

The following examples are meant to provide a listing of parameters which can facilitate the sealing method of the present invention. Many of the bag/specimen parameters can be identified and the corresponding operational parameters (vacuum pressure setting, time, etc.) can be automatically input to the sealing system via a relational database to limit the amount of steps which are required to be taken by an operator at the laboratory evaluation site.

EXAMPLE 1

4 inch diameter core (fine aggregate composition)

Specimen thickness
Vacuum pressure setting
Vacuum time
Sealing time
Exhaust time
Bag thickness
Bag material
Overall bag size -continued Reinforcement type
Bag density correction factor
Material specimen specific gravity estimate

EXAMPLE 2

4 inch diameter core (coarse aggregate composition)

Figure 12:
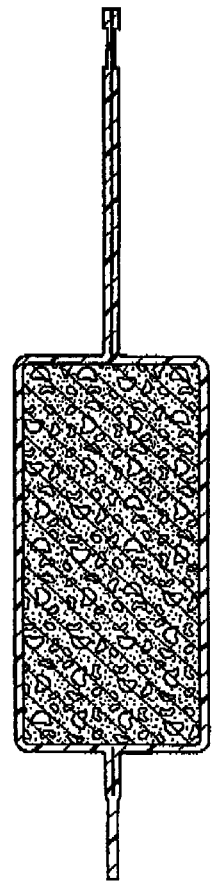
FIG. 12 is a side section view of a porous material specimen having a surface conformal jacket provided by a compressible resilient bag with one end having a longer length from the sealing edge to the specimen compared to the other end according to the present invention.
Figure 13:
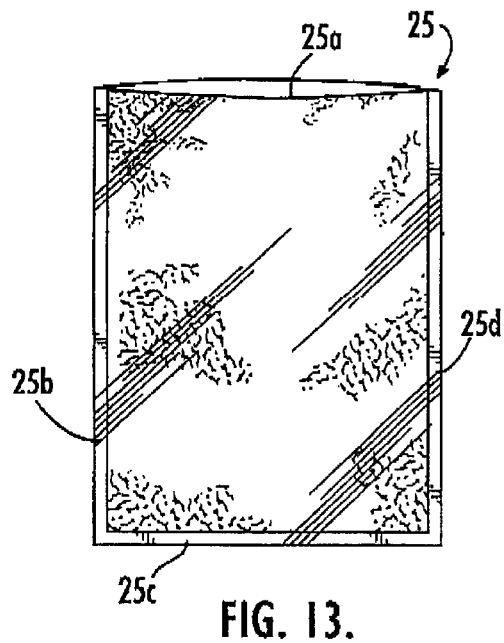
FIG. 13 is a top view illustrating a preformed bag having three pre-sealed edges or sides according to the present invention.

Specimen thickness
Vacuum pressure setting
Vacuum time
Sealing time
Exhaust time
Bag thickness
Bag material
Overall bag size
Reinforcement type
Bag density correction factor
Material specimen specific gravity estimate If the sealed specimen 125 (FIG. 12) will be stored prior to water displacement evaluation, especially for extended periods, it is preferred that the material be selected to provide an oxygen resistant barrier to minimize the oxygen migration into the chamber 29 or porous channels of the specimen. Because of the pressure differential, air may migrate across the walls of the bag into the sealed specimen 125 over time. This oxygen-resistant barrier can be provided by one or more of sizing the thickness of the wall of the material sufficiently thick to inhibit the migration of oxygen thereacross, using several layers of material, or using material to form the walls which is resistant to the migration of oxygen therethrough. Examples of oxygen resistant materials include, but are not limited to, metallized bags an/or nylon bags.

In summary, the instant invention allows for a reliable method to seal a porous compacted material specimen which can provide accurate measurement results for density measurements using water or liquid displacement tests. Advantageously, the apparatus, system and methods of the instant invention can reduce the variation attributed to operators by making the method essentially independent of operator material trimming and custom application. The sealing method is consistent across specimens and similar bags are configured to displace the same volume of water. Further, the sealed sample is easily removed from the seal and the specimen can undergo further evaluation because it's material properties remain intact. Still further, the instant invention can be used across a plurality of specimen composite mixes without requiring standard reference block density correction factors at the laboratory for each compacted specimen evaluated.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures.

Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A sample specimen configuration for sealing a dense material sample to inhibit liquid contacting the sample during specific gravity and/or density measurements using liquid displacement tests, comprising:
   a preformed resilient bag having at least one sealed side and one opening formed therein and defining a holding chamber; and
   a compacted material sample having an exterior surface contour positioned in said chamber of said preformed resilient bag;
   wherein said preformed bag has a first non-sealed configuration and a second sealed configuration, and wherein in said second sealed configuration said preformed bag is configured to substantially conform to said sample's exterior surface contour, and
wherein said preformed bag has a length and a width which are at least about 40% longer than the longest dimension of the compacted material sample.

2. A sample specimen configuration for sealing a dense material sample to inhibit liquid contacting the sample during specific gravity and/or density measurements using liquid displacement tests, comprising:
   a preformed resilient bag having at least one sealed side and one opening formed therein and defining a holding chamber; and
   a compacted material sample having an exterior surface contour positioned in said chamber of said preformed resilient bag;
   wherein said preformed bag has a first non-sealed configuration and a second sealed configuration, and wherein in said second sealed configuration said preformed bag is configured to substantially conform to said sample's exterior surface contour, and
   wherein said preformed bag includes two opposing major internal surfaces, and wherein at least one of said major internal surfaces includes a plurality of air channels formed thereon.

3. A sample specimen configuration according to claim 2, wherein said preformed bag includes at least one material reinforced region.

4. A sample specimen configuration according to claim 3, wherein said preformed bag includes a first wall and a second opposing wall, and wherein said first and second walls define four corresponding sides, and wherein said preformed bag is co-joined along three of said four corresponding sides at a production site remote from the sealing site and said at least one opening is a single opening defined by non-joined corresponding portions of said fourth side.

5. A sample specimen configuration according to claim 4, wherein said preformed bag includes four perimeter sides with laterally outwardly extending edge portions, and wherein said at least one opening is defined by the unsealed edge portions of at least one of said four perimeter sides.

6. A system according to claim 1, wherein said preformed bag comprises a plurality of material layers.

7. A system according to claim 1, wherein said preformed bag and said compacted material sample are positioned inside a second preformed bag, and wherein in said second sealed configuration, said first and second preformed bags are configured to substantially conform to said material sample's exterior surface contour.

8. A system according to claim 1, wherein said compacted material sample comprises at least one of compacted soil, concrete, compacted aggregate, compacted asphalt, bituminous material, and solid core samples.

9. An apparatus for sealing a specimen, comprising:
   a preformed resilient bag defining a holding chamber therein;
   a compacted material sample having an exterior surface contour positioned in said chamber of said preformed resilient bag, wherein said preformed bag has a first non-sealed configuration and a second sealed configuration, and wherein in said second sealed configuration said preformed bag is configured to encase and substantially conform about said sample's exterior surface contour; and
   a vacuum apparatus operably associated with said preformed bag with said compacted material sample, wherein said vacuum apparatus includes an air chamber with a vacuum channel which is operably associated with a vacuum pump and a flow rate adjustable exhaust port, and wherein, in operation, said bag is positioned in said chamber and said preformed bag collapses to conform to said sample's exterior contour surface responsive to the controlled introduction of air into said exhaust port, said controlled introduction extending at least about thirty seconds.

10. An apparatus according to claim 9, wherein said bag includes a perimeter with four sides and at least one opening formed therein along at least one edge portion of one of said four sides, and said apparatus further comprises sealing means for sealing said at least one opening of said preformed bag in said second configuration, and wherein said preformed bag has a length and a width which are at least about 40% longer than the longest dimension of the compacted material sample.

11. An apparatus according to claim 9, wherein said vacuum includes a vacuum chamber which is sized and configured to hold said preformed bag and said sample therein.

12. An apparatus for sealing a material specimen for a liquid density evaluation, comprising:
   a preformed resilient bag defining a holding chamber therein;
   a compacted material sample having an exterior surface contour positioned in said chamber of said preformed resilient bag, wherein said preformed bag has a first non-sealed configuration and a second sealed configuration, and wherein in said second sealed configuration said preformed bag is configured to encase and substantially conform about said sample's exterior surface contour; and
   a vacuum apparatus operably associated with said preformed bag with said compacted material sample, wherein said bag includes four sides with edges and at least one opening formed along one edge portion thereof, wherein said vacuum chamber includes a laterally extending portion which is configured to receive said open portion of said bag therein such that a major portion of said bag and said sample are excluded from said chamber.

13. An apparatus according to claim 11, wherein said vacuum chamber includes at least one heating element positioned therein for sealing each of said at least one openings of said bag.

14. An apparatus according to claim 12, wherein said vacuum chamber includes at least one heating element positioned therein for sealing each of said at least one openings of said bag.

15. An apparatus according to claim 9, wherein the apparatus has an evacuation mode, a sealing mode for activating the heating element, and an exhaust mode, the exhaust mode corresponding to the introduction of air into the chamber after the evacuation mode, the apparatus further comprising computer program code for automatically directing the timing, sequence, and duration of the three modes and the rate of evacuation and exhaust corresponding to one or more of the type of bag and the sample type being sealed.

16. A method for preparing a compacted material specimen sample for liquid displacement testing, comprising the steps of:
   providing a preformed compressible bag with predetermined dimensions, said bag having a perimeter with sides, wherein a portion of said perimeter has an open portion formed therein such that it is unsealed, and wherein said perimeter sides have lengths which are at least about 40% longer than the longest dimension of a material specimen to undergo analysis;
   then subsequently inserting the material specimen into the bag;
   encasing said material specimen within said bag such that a portion of said bag substantially conforms to the exterior profile of the material specimen held therein, wherein said encasing step comprises positioning the material specimen in the unsealed bag in a vacuum chamber, evacuating the unsealed bag in the vacuum chamber, sealing said open portion of the bag, and after sealing, controllably directing air back into the vacuum chamber to return the pressure therein to ambient atmospheric pressure to thereby form an encased specimen suitable for liquid displacement testing.

17. A method according to claim 16, wherein said preformed bag includes a plurality of air channels formed on an internally oriented major surface.

18. A method according to claim 16, wherein said bag has a perimeter width and length of about 10 by 16 inches, respectively, wherein said preformed bag includes overlying walls having corresponding perimeters, and wherein said overlying walls are joined along a major portion of the perimeters to define outwardly extending edge portions.

19. A method according to claim 16, wherein said method further comprises the step of attaching reinforcement patches to at least one of the internal major surfaces of said bag and one or more ends of said material specimen.

20. A method according to claim 16, wherein said bag is produced at a first site, and said inserting and sealing steps are performed at a second site which is remote and physically separate from the first site.

21. A method according to claim 16, wherein said controllably directing step is performed with a controlled air flow rate to inhibit the abrupt introduction of air into said chamber, and wherein said directing step has a duration of at least about 30 seconds.

22. A method according to claim 16, wherein said directing step is automatically driven with a predetermined time and air flow rate which is selected to control the exhaust pressure corresponding to one or more of the size of bag and type of specimen held therein.

23. A method according to claim 16, wherein said material specimen comprises at least one of compacted soil, concrete, compacted aggregate, compacted asphalt, bituminous material, and solid core materials.

24. A reproducible puncture resistant water jacket for a material specimen for use in water displacement density or specific gravity tests, comprising:
   a first preformed resilient bag structure having at least two co-joined sides, wherein said resilient bag structure is sized and configured to receive a compacted material specimen having an external surface therein, wherein said bag structure has a first open configuration and a second sealed configuration such that when in said second sealed configuration said bag structure includes a portion which substantially conforms to said external surface of said specimen, and wherein said bag structure is produced at a first site and sealed closed at a second site which is remote and physically separate from the first site, the second site being associated with liquid displacement testing,
   wherein said bag structure is configured to be manufactured in mass production under precision tolerance limits such that the dimensions and configuration are suitably controlled during manufacturing to thereby provide a substantially constant water displacement volume for a material specimen type when subjected to water displacement measurements of dense material specimens, and wherein, and wherein said preformed bag has a length and a width which are at least about 40% longer than the longest dimension of the compacted material sample.

25. A reproducible puncture resistant water jacket according to claim 24, in combination with a dense material specimen, wherein said material specimen comprises at least one of compacted soil, concrete, compacted aggregate, compacted asphalt, bituminous material, and solid core materials.

26. A reproducible puncture resistant water jacket according to claim 24, wherein said preformed bag structure comprises first and second overlying material layers defining first and second opposing walls defining four perimeter sides and a chamber for receiving the dense material specimen therebetween, wherein said preformed bag structure is configured such that three of said perimeter sides are conjoined in said first open configuration, and wherein each of said perimeter sides has a length of at least about 10 inches.

27. A reproducible puncture resistant water jacket according to claim 24, wherein said preformed bag structure comprises first and second overlying material layers defining first and second opposing walls defining a perimeter and a chamber for receiving the dense material specimen therebetween, wherein said preformed bag structure is configured such that a major portion of said perimeter includes co-joined segments of said first and second opposing walls in said first open configuration, and wherein each of said perimeter sides has a length of at least about 10 inches.

28. A reproducible puncture resistant water jacket according to claim 27, wherein said first and second material layers comprise materials which are substantially impermeable to oxygen.

29. A reproducible puncture resistant water jacket according to claim 28, wherein said first and second layers include reinforcement patches.

30. A reproducible puncture resistant water jacket according to claim 24, wherein said preformed bag structure comprises walls formed of at least one of metallocene catalyzed polyolefin and a polymer comprising at least about 20% nylon.

31. A reproducible puncture resistant water jacket according to claim 27, wherein at least one of said first and second material layers includes air channels formed therein.

32. A reproducible puncture resistant water jacket according to claim 24, further comprising a second preformed resilient bag structure having at least two co-joined sides, wherein said second resilient bag structure is sized and configured to receive a said first preformed bag and compacted material specimen therein, and wherein said first and second preformed bag structures have a first open configuration and a second sealed configuration such that when in said second sealed configuration each of said bag structures include a portion which is substantially conformal to said external surface of said specimen, and wherein said first and second bag structures are produced at a first site and sealed closed at a second site remote from said first site.

33. A reproducible puncture resistant water jacket according to claim 24, wherein said preformed bag structure includes at least one sealed edge which extends laterally outward relative to the material specimen receiving portion of said bag structure.

34. A method for immersing a compacted mixture in a liquid displacement bath for determining the specific gravity of specimens comprising the steps of:
inserting a material specimen having an exterior surface into at least one bag having at least one open side;
positioning the bag with the material specimen inside a vacuum chamber;
evacuating the chamber after said positioning step;
sealing the bag to enclose the material specimen therein;
increasing the pressure in the evacuated vacuum chamber after said sealing step in a controlled manner such that the pressure is gradually increased over at least about 30 seconds thereby forcing said bag to collapse such that a portion of the bag conforms to the exterior contour of the material specimen held therein thereby encasing the material specimen;
placing the sealed specimen in a liquid displacement bath; and
measuring the volume of displaced water associated with said placing step.

35. A method according to claim 34, further comprising the step of adjusting the measured volume of liquid displaced by the bag in isolation of the specimen thereby providing an adjustment factor which is used in the determination of the specific gravity associated with the material specimen.

36. A method according to claim 34, wherein the bag has a perimeter with four sides, each of the sides having a length of at least about 10 inches, and wherein said method steps are repeated for a plurality of specimens.

37. A method according to claim 35, further comprising a step of accounting for the volume of liquid displaced by the bag with a reference standard having a known density in isolation of a material specimen thereby providing a standard adjustment factor which is used to determine the specific gravity associated with multiple material specimens and a corresponding plurality of bags.

38. A method according to claim 34, wherein the material specimen is configured with a coarse external surface.

39. A method according to claim 34, wherein said bag comprises a material which is resilient and puncture resistant.

40. A method according to claim 34, wherein said bag comprises at least about 20% nylon.

41. A method according to claim 35, wherein said bag comprises reinforced regions.

42. A method according to claim 36, wherein said bag includes walls formed by multiple layers of material.

43. A method according to claim 34, wherein said step of increasing the pressure is performed at predetermined rates corresponding to one or more of the specimen size and type.

44. A method according to claim 34, wherein said at least one bag comprises first and second bags, and wherein said first and second bag walls are formed of multiple layers of material.

45. A method according to claim 44, wherein said walls comprise a layer of a first material and an overlying layer of a second material different from said first material, wherein said first and second layers are concurrently responsive to the application of pressure.

46. A method according to claim 34, further comprising the step of establishing standardized bag density values for a plurality of material specimen thicknesses at a given vacuum operation by measuring the variation of the bag density with a plurality of standard aluminum specimens having a known density in a liquid displacement test, each standard aluminum specimen having a different thickness, and establishing a relationship for bag density which increases with the thickness of the material specimen undergoing evaluation, thereby providing a derived correction factor which can be applied during subsequent use of the bag across actual material specimens of different thickness undergoing liquid displacement testing.

47. An encased sample, resilient container for a porous material sample, comprising;
a first layer of a first material, said first layer including a first perimeter portion and a thickness of about 0.006 inches;
a second layer of a second material configured to overlay said first layer, said second layer including a second perimeter portion corresponding to said first perimeter portion and a thickness of about 0.006 inches, wherein said first and second perimeter portions are co-joined along a major portion thereof defining an internal compressible chamber therebetween and edge portions which extend laterally outward from said chamber; and
a compacted material specimen held in said chamber;
wherein said first and second layers are formed of a resilient material such that said chamber has a first collapsed position and a second non-collapsed position, said collapsed position corresponding to said chamber being sealed with said compacted material specimen positioned therein.

48. A resilient container according to claim 47, wherein said first and second layer materials are selected to provide at least one of oxygen-resistant shielding and puncture resistance for said chamber, and wherein said perimeter sides have a length of at least about 10 inches.

49. A method of preparing a porous sample for use in a water displacement evaluation, comprising the steps of:
inserting a porous sample having an exterior profile into a preformed bag;
positioning the preformed bag with the porous sample in a vacuum chamber;
evacuating the air from the chamber;
sealing the preformed bag with the sample enclosed therein, thereby providing a sealed sample; and
then exhausting the chamber to increase the pressure in the chamber in a controlled manner for at least about 30 seconds, thereby collapsing the preformed bag such that a major portion of the bag contacts the exterior profile of the porous sample.

50. A method according to claim 49, wherein said air evacuation step is performed prior to said sealing step, and said exhausting step is performed subsequent to said sealing step, and wherein said evacuating and exhausting steps are performed at predetermined times and pressures.

51. A method according to claim 49, wherein said sample is an absorptive compacted bituminous asphalt sample.

52. A method according to claim 49, wherein said sample comprises compacted soil.

53. A method according to claim 49, wherein said sample comprises concrete.

54. A method according to claim 49, wherein said sample comprises aggregate.

55. A method according to claim 49, wherein said sealing step is performed without trimming excess material from said preformed bag.

56. A method according to claim 49, wherein said preformed bag comprises a polymer material.

57. A method according to claim 56, wherein said preformed bag includes first and second walls, and wherein at least one of said first and second walls comprises a plurality of air channels thereon.

58. A method according to claim 49, further comprising the step of removing the porous sample from the sealed bag subsequent to said sealing step, wherein said sealing step preserves the integrity of the porous sample such that after said removing step the sample is available for subsequent material evaluations.

59. A computer program product for sealing a material specimen in a preformed bag, the computer program product comprising:

a computer readable storage medium having computer readable program code means embodied in said medium, said computer-readable program code means comprising:

computer readable program code means for accepting user input information associated with identifying the material specimen to be sealed in a preformed bag;

computer readable program code means for comparing the identified material specimen with predetermined operating parameters for directing the operation of a vacuum apparatus operably associated with the preformed bag holding the material specimen; and computer readable program code means for directing the operation of the vacuum apparatus corresponding to the operating parameters associated with the identified material specimen to substantially conform a portion of the preformed bag to the exterior shape of the material specimen.

60. A computer program product according to claim 59, further comprising computer readable program code means for accepting user input information associated with the identification of the preformed bag being sealed.

61. A computer program product according to claim 59, further comprising computer readable program code means for providing a preformed bag adjustment number for use in specific gravity or density measurement calculations associated with water displacement tests.

62. A computer program product according to claim 59, wherein said computer readable program code means for comparing the material specimen with predetermined operating parameters includes providing an optimum operating pressure selected to correspond to one or more of the bag density and the density of the identified material specimen.

63. A computer program product according to claim 59, further comprising computer readable program code means for calculating the specific gravity of the material specimen and printing the result of the calculated specific gravity of the material specimen.

64. A computer program product according to claim 63, wherein said computer readable program code means for calculating the specific gravity of the specimen includes a look-up table or calculated reference value associated with the bag density when used with a particular material specimen configuration and thickness.

65. A liquid displacement testing system, comprising:

a vacuum apparatus having an internal vacuum chamber;

a first scale positioned in said vacuum apparatus such that it can provide a dry air weight measure of a sealed specimen held therein;

a liquid displacement bath;

a second scale operably associated with said liquid displacement bath; and computer means operably associated with said first scale, said vacuum apparatus, and said second scale, said computer means including a computer program product having computer readable program code means for calculating the specific gravity of a compacted material specimen corresponding to data directly input into said computer means from said first and second scales.

66. A liquid displacement testing system according to claim 65, wherein said first and second scale are the same scale.

\* \* \* \* \*